US008998923B2

(12) United States Patent
Chirico et al.

(10) Patent No.: US 8,998,923 B2
(45) Date of Patent: Apr. 7, 2015

(54) THREADED BONE FILLING MATERIAL PLUNGER

(75) Inventors: Paul E. Chirico, Campbell, CA (US); Ben M. Chan, Fremont, CA (US); Peter G. Knopp, Pleasanton, CA (US)

(73) Assignee: Spinealign Medical, Inc., San Jose, CA (US)

( * ) Notice: Subject to any disclaimer, the term of this patent is extended or adjusted under 35 U.S.C. 154(b) by 170 days.

(21) Appl. No.: 12/476,858

(22) Filed: Jun. 2, 2009
(Under 37 CFR 1.47)

(65) Prior Publication Data

US 2010/0069913 A1    Mar. 18, 2010

Related U.S. Application Data

(60) Provisional application No. 61/058,187, filed on Jun. 2, 2008.

(51) Int. Cl.
*A61B 17/58* (2006.01)
*A61B 17/60* (2006.01)
*A61F 2/00* (2006.01)
*A61B 17/16* (2006.01)
(Continued)

(52) U.S. Cl.
CPC .......... *A61B 17/1655* (2013.01); *A61B 17/1617* (2013.01); *A61B 17/1671* (2013.01); *A61B 17/8858* (2013.01); *A61B 17/686* (2013.01); *A61B 17/7032* (2013.01); *A61B 17/8685* (2013.01); *A61B 17/8847* (2013.01); *A61B 2017/00867* (2013.01)

(58) Field of Classification Search
USPC ................................. 606/105, 310, 326, 327
See application file for complete search history.

(56) References Cited

U.S. PATENT DOCUMENTS

| 817,973 A | 4/1906 | Hausmann |
|---|---|---|
| 2,072,346 A | 3/1937 | Smith |

(Continued)

FOREIGN PATENT DOCUMENTS

| EP | 1582159 A1 | 10/2005 |
|---|---|---|
| EP | 1582161 A1 | 10/2005 |

(Continued)

OTHER PUBLICATIONS

Chirico et al.; U.S. Appl. No. 12/650,851 entitled "Self-expanding bone stabilization devices," filed Dec. 31, 2009.

(Continued)

*Primary Examiner* — Andrew Yang
(74) *Attorney, Agent, or Firm* — Shartsis Friese LLP; Cecily Anne O'Regan

(57) ABSTRACT

Described herein are devices, systems and method for assuring that connection regions (e.g., threaded regions) of stabilization devices are clear of bone filling materials such as bone cements. A stabilization device may be referred to as a bone stabilization device or an anchor, and may be a self-expanding device configured for insertion into bone. One exemplary clearing device is configured as a plunger-type device for clearing the connector region by scraping and/or rubbing the surface of the connector region. A clearing device may include a handle, a rod and a connector end that is configured to mate with the connector of a stabilization device. The connector end may include one or more scraping surfaces (e.g., edges) and may include a vacuum port for removing material such as scraped bone cement.

20 Claims, 25 Drawing Sheets

(51) Int. Cl.
*A61B 17/88* (2006.01)
*A61B 17/68* (2006.01)
*A61B 17/70* (2006.01)
*A61B 17/86* (2006.01)
*A61B 17/00* (2006.01)

(56) References Cited

U.S. PATENT DOCUMENTS

| | | |
|---|---|---|
| 3,174,387 A | 3/1965 | Fischer |
| 3,320,957 A | 5/1967 | Sokolik |
| 3,517,128 A | 6/1970 | Hines |
| 3,678,925 A | 7/1972 | Fischer et al. |
| 3,779,239 A | 12/1973 | Fischer et al. |
| 3,896,504 A | 7/1975 | Fischer |
| 4,013,071 A | 3/1977 | Rosenberg |
| 4,274,324 A | 6/1981 | Giannuzzi |
| 4,394,370 A | 7/1983 | Jefferies |
| 4,472,840 A | 9/1984 | Jefferies |
| 4,632,101 A | 12/1986 | Freedland |
| 4,711,232 A | 12/1987 | Fischer et al. |
| 4,716,893 A | 1/1988 | Fischer et al. |
| 4,760,843 A | 8/1988 | Fischer et al. |
| 4,828,439 A | 5/1989 | Giannuzzi |
| 4,969,887 A | 11/1990 | Sodhi |
| 4,969,888 A | 11/1990 | Scholten et al. |
| 5,004,454 A | 4/1991 | Beyar et al. |
| 5,059,193 A | 10/1991 | Kuslich |
| 5,062,851 A | 11/1991 | Branemark |
| 5,074,871 A | 12/1991 | Groshong |
| 5,108,404 A | 4/1992 | Scholten et al. |
| 5,108,443 A | 4/1992 | Branemark |
| 5,113,846 A | 5/1992 | Hiltebrandt et al. |
| 5,163,961 A | 11/1992 | Harwin |
| 5,171,284 A | 12/1992 | Branemark |
| 5,176,709 A | 1/1993 | Branemark |
| 5,209,753 A | 5/1993 | Biedermann |
| 5,246,445 A | 9/1993 | Yachia et al. |
| 5,284,655 A | 2/1994 | Bogdansky et al. |
| 5,314,476 A | 5/1994 | Prewett et al. |
| 5,326,205 A | 7/1994 | Anspach, Jr. et al. |
| 5,372,600 A | 12/1994 | Beyar et al. |
| 5,405,390 A | 4/1995 | O'Leary et al. |
| 5,454,365 A | 10/1995 | Bonutti |
| 5,501,695 A | 3/1996 | Anspach, Jr. et al. |
| 5,510,396 A | 4/1996 | Prewett et al. |
| 5,702,215 A | 12/1997 | Li |
| 5,713,904 A | 2/1998 | Errico et al. |
| 5,725,541 A | 3/1998 | Anspach, III et al. |
| 5,782,838 A | 7/1998 | Beyar et al. |
| 5,782,865 A | 7/1998 | Grotz |
| 5,827,285 A | 10/1998 | Bramlet |
| 5,885,258 A | 3/1999 | Sachdeva et al. |
| 5,951,288 A | 9/1999 | Sawa |
| 5,964,771 A | 10/1999 | Beyar et al. |
| 5,968,078 A | 10/1999 | Grotz |
| 5,972,000 A | 10/1999 | Beyar et al. |
| 5,976,139 A | 11/1999 | Bramlet |
| 5,984,969 A | 11/1999 | Matthews et al. |
| 6,001,102 A | 12/1999 | Barbera Alacreu |
| 6,090,115 A | 7/2000 | Beyar et al. |
| 6,127,597 A | 10/2000 | Beyar et al. |
| 6,149,669 A | 11/2000 | Li |
| 6,162,234 A | 12/2000 | Freedland et al. |
| 6,183,474 B1 | 2/2001 | Bramlet et al. |
| 6,235,043 B1 | 5/2001 | Reiley et al. |
| 6,287,336 B1 | 9/2001 | Globerman et al. |
| 6,328,744 B1 | 12/2001 | Harari et al. |
| 6,328,758 B1 | 12/2001 | Tornier et al. |
| 6,332,885 B1 | 12/2001 | Martella |
| 6,334,446 B1 | 1/2002 | Beyar |
| 6,334,871 B1 | 1/2002 | Dor et al. |
| 6,340,477 B1 | 1/2002 | Anderson |
| 6,371,953 B1 | 4/2002 | Beyar et al. |
| 6,371,979 B1 | 4/2002 | Beyar et al. |
| 6,382,214 B1 | 5/2002 | Raz et al. |
| 6,387,041 B1 | 5/2002 | Harari et al. |
| 6,402,777 B1 | 6/2002 | Globerman et al. |
| 6,406,480 B1 | 6/2002 | Beyar et al. |
| 6,440,138 B1 | 8/2002 | Reiley et al. |
| 6,500,182 B2 | 12/2002 | Foster |
| 6,502,578 B2 | 1/2003 | Raz et al. |
| 6,544,273 B1 | 4/2003 | Harari et al. |
| 6,554,833 B2 | 4/2003 | Levy et al. |
| 6,575,984 B2 | 6/2003 | Beyar |
| 6,575,998 B2 | 6/2003 | Beyar |
| 6,579,290 B1 | 6/2003 | Hardcastle et al. |
| 6,582,453 B1 | 6/2003 | Tran et al. |
| 6,592,610 B2 | 7/2003 | Beyar |
| 6,599,295 B1 | 7/2003 | Tornier et al. |
| 6,635,058 B2 | 10/2003 | Beyar et al. |
| 6,641,587 B2 | 11/2003 | Scribner et al. |
| 6,663,642 B2 | 12/2003 | Beyar et al. |
| 6,668,688 B2 | 12/2003 | Zhao et al. |
| 6,673,094 B1 | 1/2004 | McDevitt et al. |
| 6,676,665 B2 | 1/2004 | Foley et al. |
| 6,679,886 B2 | 1/2004 | Weikel et al. |
| 6,691,711 B2 | 2/2004 | Raz et al. |
| 6,716,216 B1 | 4/2004 | Boucher et al. |
| 6,730,110 B1 | 5/2004 | Harari et al. |
| 6,733,506 B1 | 5/2004 | McDevitt et al. |
| 6,740,093 B2 | 5/2004 | Hochschuler et al. |
| 6,746,451 B2 | 6/2004 | Middleton et al. |
| 6,746,455 B2 | 6/2004 | Beyar et al. |
| 6,843,796 B2 | 1/2005 | Harari et al. |
| 6,981,981 B2 | 1/2006 | Reiley et al. |
| 7,097,648 B1 | 8/2006 | Globerman et al. |
| 7,153,306 B2 | 12/2006 | Ralph et al. |
| 7,166,121 B2 | 1/2007 | Reiley et al. |
| 2001/0031981 A1 | 10/2001 | Evans et al. |
| 2001/0041930 A1 | 11/2001 | Globerman et al. |
| 2001/0049531 A1 | 12/2001 | Reiley et al. |
| 2001/0053913 A1 | 12/2001 | Freedland |
| 2002/0016583 A1 | 2/2002 | Cragg |
| 2002/0045917 A1 | 4/2002 | Ambrisco et al. |
| 2002/0072753 A1 | 6/2002 | Cohen |
| 2002/0095181 A1 | 7/2002 | Beyar |
| 2002/0146398 A1 | 10/2002 | Vago et al. |
| 2002/0165544 A1 | 11/2002 | Perren et al. |
| 2002/0198532 A1 | 12/2002 | Michelson |
| 2003/0065396 A1 | 4/2003 | Michelson |
| 2003/0135225 A1 | 7/2003 | Harari et al. |
| 2003/0135279 A1 | 7/2003 | Michelson |
| 2003/0149482 A1 | 8/2003 | Michelson |
| 2003/0153916 A1 | 8/2003 | Michelson |
| 2004/0049197 A1 | 3/2004 | Barbera Alacreu |
| 2004/0049280 A1 | 3/2004 | Cauthen |
| 2004/0097927 A1 | 5/2004 | Yeung et al. |
| 2004/0133204 A1 | 7/2004 | Davies |
| 2004/0153064 A1 | 8/2004 | Foley et al. |
| 2004/0158246 A1 | 8/2004 | Assaker et al. |
| 2004/0167625 A1 | 8/2004 | Beyar et al. |
| 2004/0193215 A1 | 9/2004 | Harari et al. |
| 2004/0210217 A1 | 10/2004 | Baynham et al. |
| 2004/0215344 A1 | 10/2004 | Hochschuler et al. |
| 2004/0220573 A1 | 11/2004 | McDevitt et al. |
| 2004/0230193 A1 | 11/2004 | Cheung et al. |
| 2005/0004424 A1 | 1/2005 | Raz et al. |
| 2005/0004426 A1 | 1/2005 | Raz et al. |
| 2005/0055027 A1 | 3/2005 | Yeung et al. |
| 2005/0069397 A1 | 3/2005 | Shavit et al. |
| 2005/0070911 A1 | 3/2005 | Carrison et al. |
| 2005/0090852 A1 | 4/2005 | Layne et al. |
| 2005/0113836 A1 | 5/2005 | Lozier et al. |
| 2005/0119617 A1 | 6/2005 | Stecker et al. |
| 2005/0143734 A1 | 6/2005 | Cachia et al. |
| 2005/0143827 A1 | 6/2005 | Globerman et al. |
| 2005/0182418 A1 | 8/2005 | Boyd et al. |
| 2005/0240188 A1 | 10/2005 | Chow et al. |
| 2005/0278036 A1 | 12/2005 | Leonard et al. |
| 2005/0288678 A1 | 12/2005 | Reiley et al. |
| 2006/0004455 A1 | 1/2006 | Leonard et al. |
| 2006/0004458 A1 | 1/2006 | Collins et al. |
| 2006/0009778 A1 | 1/2006 | Collins et al. |
| 2006/0009851 A1 | 1/2006 | Collins et al. |

(56) References Cited

U.S. PATENT DOCUMENTS

| | | |
|---|---|---|
| 2006/0058880 A1 | 3/2006 | Wysocki et al. |
| 2006/0079905 A1 | 4/2006 | Beyar et al. |
| 2006/0084998 A1 | 4/2006 | Levy et al. |
| 2006/0106459 A1 | 5/2006 | Truckai et al. |
| 2006/0116689 A1 | 6/2006 | Albans et al. |
| 2006/0184192 A1 | 8/2006 | Markworth et al. |
| 2006/0235391 A1 | 10/2006 | Sutterlin, III |
| 2006/0235410 A1 | 10/2006 | Ralph et al. |
| 2006/0235417 A1 | 10/2006 | Sala |
| 2006/0235520 A1 | 10/2006 | Pannu |
| 2006/0247648 A1 | 11/2006 | Serbousek |
| 2006/0271061 A1 | 11/2006 | Beyar et al. |
| 2007/0032567 A1 | 2/2007 | Beyar et al. |
| 2007/0032790 A1 | 2/2007 | Aschmann et al. |
| 2007/0032791 A1 | 2/2007 | Greenhalgh |
| 2007/0043373 A1 | 2/2007 | Sala et al. |
| 2007/0060933 A1 | 3/2007 | Sankaran et al. |
| 2007/0067034 A1 | 3/2007 | Chirico et al. |
| 2007/0068329 A1 | 3/2007 | Phan et al. |
| 2007/0088436 A1 | 4/2007 | Parsons et al. |
| 2007/0118131 A1 | 5/2007 | Gooch |
| 2007/0135759 A1 | 6/2007 | Kraft et al. |
| 2007/0173939 A1 | 7/2007 | Kim et al. |
| 2007/0198023 A1 | 8/2007 | Sand et al. |
| 2007/0198043 A1 | 8/2007 | Cox et al. |
| 2007/0219634 A1 | 9/2007 | Greenhalgh et al. |
| 2007/0244485 A1 | 10/2007 | Greenhalgh et al. |
| 2007/0282442 A1 | 12/2007 | Malandain et al. |
| 2007/0282443 A1 | 12/2007 | Globerman et al. |
| 2008/0039893 A1 | 2/2008 | McLean et al. |
| 2008/0281364 A1 | 11/2008 | Chirico et al. |
| 2008/0294204 A1 | 11/2008 | Chirico et al. |
| 2009/0005782 A1 | 1/2009 | Chirico et al. |
| 2009/0005821 A1 | 1/2009 | Chirico et al. |
| 2009/0012564 A1 | 1/2009 | Chirico et al. |

FOREIGN PATENT DOCUMENTS

| | | |
|---|---|---|
| EP | 1815813 A2 | 8/2007 |
| EP | 1820462 A1 | 8/2007 |
| FR | 2653006 A | 4/1991 |
| WO | WO 91/16005 A1 | 10/1991 |
| WO | WO 94/16629 A1 | 8/1994 |
| WO | WO 94/22379 A1 | 10/1994 |
| WO | WO 94/26174 A1 | 11/1994 |
| WO | WO 95/31941 A1 | 11/1995 |
| WO | WO 96/12436 A1 | 5/1996 |
| WO | WO 96/26682 A1 | 9/1996 |
| WO | WO97/18769 A1 | 5/1997 |
| WO | WO 97/33534 A1 | 9/1997 |
| WO | WO 98/22159 A2 | 5/1998 |
| WO | WO 98/38918 A1 | 9/1998 |
| WO | WO 00/40158 A2 | 7/2000 |
| WO | WO 00/44319 A1 | 8/2000 |
| WO | WO 00/44321 A2 | 8/2000 |
| WO | WO 00/44946 A1 | 8/2000 |
| WO | WO 00/74578 A2 | 12/2000 |
| WO | WO 01/08571 A1 | 2/2001 |
| WO | WO 01/54598 A1 | 8/2001 |
| WO | WO 03/007853 A1 | 1/2003 |
| WO | WO 03/061495 A2 | 7/2003 |
| WO | WO 2004/110292 A2 | 12/2004 |
| WO | WO 2004/110300 A2 | 12/2004 |
| WO | WO 2005/032326 A2 | 4/2005 |
| WO | WO 2005/055801 A2 | 6/2005 |
| WO | WO 2005/110259 A1 | 11/2005 |
| WO | WO 2006/006169 A2 | 1/2006 |
| WO | WO 2006/011152 A2 | 2/2006 |
| WO | WO 2006/016384 A1 | 2/2006 |
| WO | WO 2006/022644 A1 | 3/2006 |
| WO | WO 2006/034436 A2 | 3/2006 |
| WO | WO 2006/037013 A1 | 4/2006 |
| WO | WO 2006/042334 A2 | 4/2006 |
| WO | WO 2006/068682 A1 | 6/2006 |
| WO | WO 2006/116760 A2 | 11/2006 |
| WO | WO 2006/116761 A2 | 11/2006 |
| WO | WO 2007/009107 A2 | 1/2007 |
| WO | WO 2007/034516 A1 | 3/2007 |
| WO | WO 2007/041665 A2 | 4/2007 |
| WO | WO/2007/067726 | 6/2007 |
| WO | WO 2007/073488 A2 | 6/2007 |
| WO | WO 2007/076308 A2 | 7/2007 |
| WO | WO 2007/076374 A2 | 7/2007 |
| WO | WO 2007/076376 A2 | 7/2007 |
| WO | WO 2007/076377 A2 | 7/2007 |
| WO | WO 2007/079237 A2 | 7/2007 |
| WO | WO 2007/084239 A2 | 7/2007 |
| WO | WO 2007/113862 A1 | 10/2007 |
| WO | WO 2007/131002 A2 | 11/2007 |

OTHER PUBLICATIONS

Souza et al.; U.S. Appl. No. 12/390,307 entitled "Interlocking handle," filed Feb. 20, 2009.

Chirico et al.; U.S. Appl. No. 12/463,262 entitled "Devices and method for bilateral support of a compression-fractured vertebral body," filed May 8, 2009.

Chirico et al.; U.S. Appl. No. 12/469,461 entitled "Systems, devices and methods for posterior lumbar interbody fusion," filed May 20, 2009.

Chirico et al.; U.S. Appl. No. 12/473,175 entitled "Implantable devices and methods for treating micro-architecture deterioration of bone tissue," filed May 27, 2009.

Knopp et al.; U.S. Appl. No. 12/504,066 entitled "Morselizer" filed Jul. 16, 2009.

Knopp et al.; U.S. Appl. No. 12/476,924 entitled "Controlled deployment handles for bone stabilization devices," Jun. 2, 2009.

SpineWave, 510(k) Summary, StaXx XD System, Apr. 27, 2006.

SpineWave, Letter from FDA regarding StaXx XD System, Apr. 27, 2006.

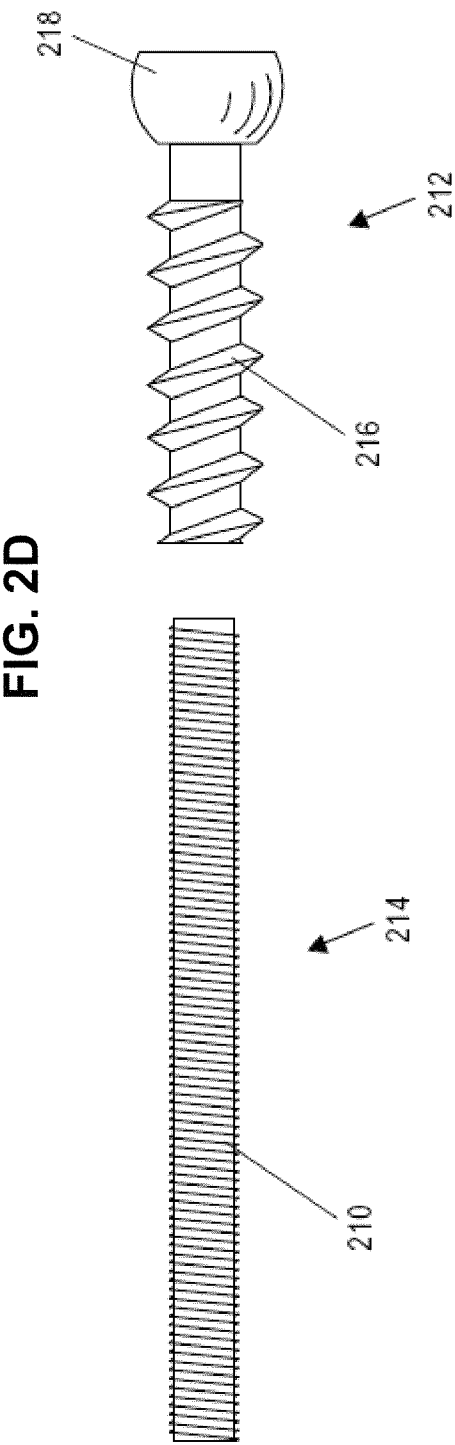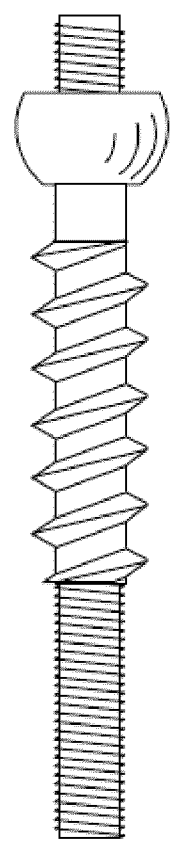
FIG. 2D
FIG. 2E

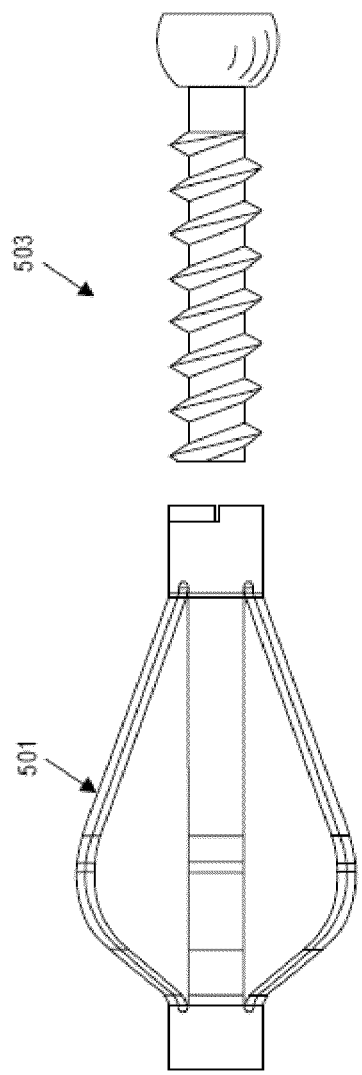

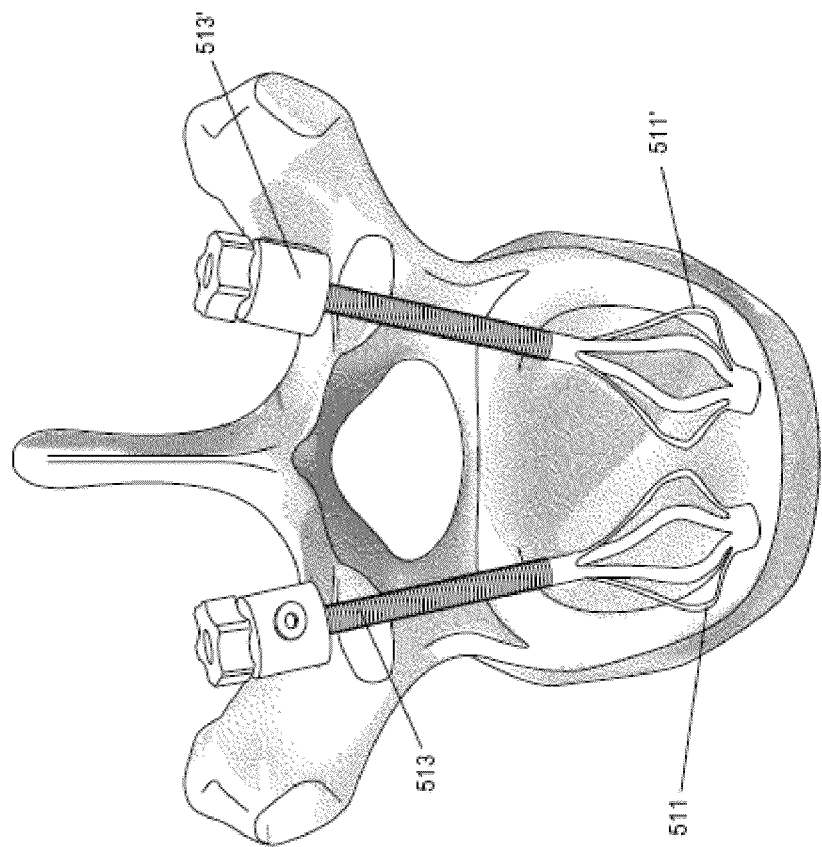

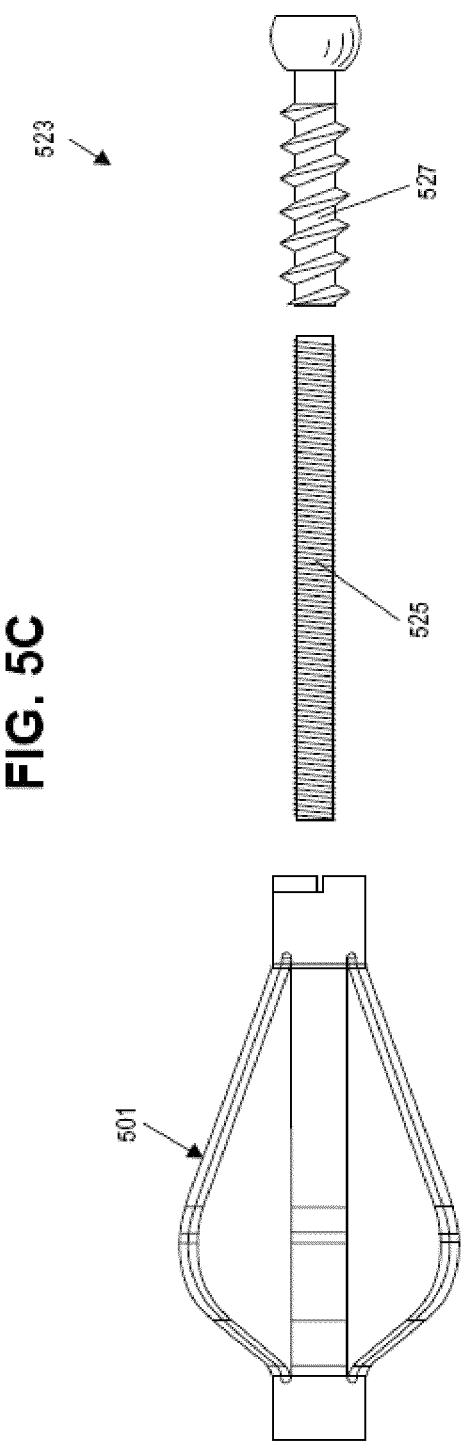

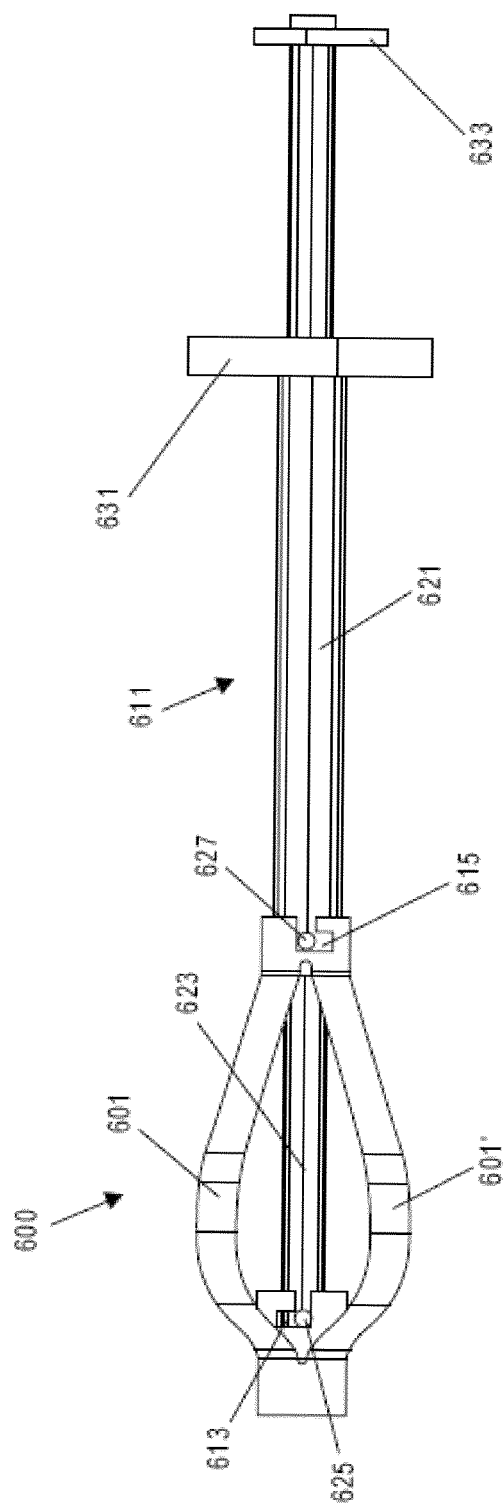

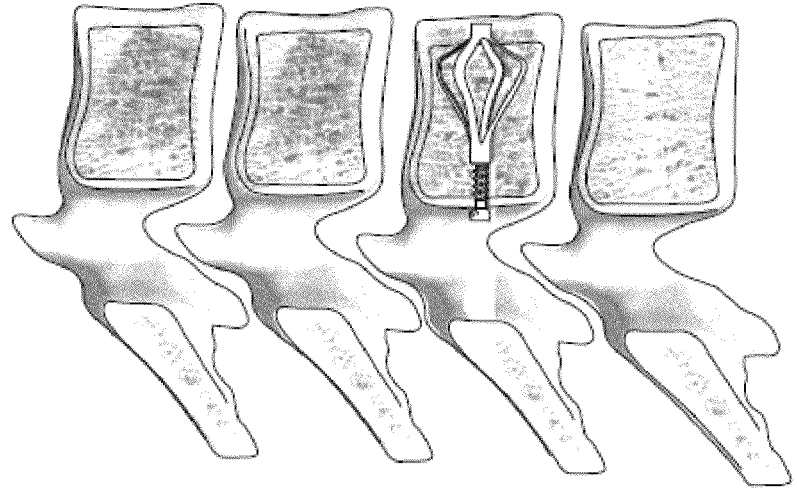
FIG. 7I
FIG. 7H

THREADED BONE FILLING MATERIAL PLUNGER

CROSS REFERENCE TO RELATED APPLICATIONS

This application claims priority to U.S. Provisional Patent Application Ser. No. 61/058,187, filed on Jun. 2, 2008 and titled "THREADED BONE FILLING MATERIAL PLUNGER."

This provisional patent application is related to U.S. patent application Ser. No. 12/025,537, titled "METHODS AND DEVICES FOR STABILIZING BONE COMPATIBLE FOR USE WITH BONE SCREWS", filed on Feb. 4, 2008. This application is also related to U.S. patent application Ser. No. 11/468,759, filed on Aug. 30, 2006, which claims the benefit of U.S. Provisional Application No. 60/713,259, filed on Aug. 31, 2005, and to U.S. Provisional Patent Application No. 60/916,731, filed on May 8, 2007. All of these applications are incorporated herein by reference in their entirety.

INCORPORATION BY REFERENCE

All publications and patent applications mentioned in this specification are herein incorporated by reference in their entirety as if each individual publication or patent application was specifically and individually indicated to be incorporated by reference.

FIELD OF THE INVENTION

Described herein are systems, devices, and methods for treating and supporting bone within a skeletal structure. The invention also relates to systems, devices, and methods for treating and supporting cancellous bone within vertebral bodies, including, but not limited to, vertebral bodies affected by osteoporosis.

BACKGROUND OF THE INVENTION

Devices and methods for supporting, fusing and expanding bone cavities may include devices and methods adapted for the use of bone cement or filler. For example, at least some of the devices described in U.S. patent application Ser. No. 12/025,537, titled "METHODS AND DEVICES FOR STABILIZING BONE COMPATIBLE FOR USE WITH BONE SCREWS", filed on Feb. 4, 2008 may be inserted into a bone, and expanded, and then filled with bone cements of any appropriate type. In many of these devices, the bone cement may be applied by injecting the material into the base of the device after it has been inserted. Unfortunately, this injection may coat or contaminate regions of the device that are adapted to be secured to other devices, including threaded bone screws, screws, connectors, or the like. For example, these devices may be used to anchor a pedicle screw. Contamination of the mating region (e.g., a threaded region) of the device with cement or other material may interfere with the mating of the device (e.g., anchor device) to other components (e.g., pedicle screws). Thus, it would be desirable to have devices, methods and/or systems for eliminating contamination by bone filler, cement or other fluent material that is applied to these devices.

Described herein are devices, systems and methods for preventing contamination of bone stabilization devices. In particular, described herein are device and methods for clearing or preventing contamination of connector regions of bone stabilization devices and anchors that may be used with bone screws including pedicle screws.

SUMMARY OF THE INVENTION

Described herein are devices, systems and method for assuring that connection regions (e.g., threaded regions) of stabilization devices are clear of bone filling materials such as bone cements. A stabilization device may be referred to as a bone stabilization device or an anchor, and are described in detail below.

The devices described herein may be referred to as devices for clearing bone stabilization device connector regions. One exemplary device described herein is configured as a threaded bone filling material plunger. This exemplary embodiment includes a handle, a rod and a connector end that is configured to mate with the connector of a stabilization device. This device may be included as part of a kit. The connector region may be a threaded region that is configured to mate with a connector on the stabilization device.

In operation, the device may be used to clear the mating region (e.g., threads) of an implanted stabilization device by mating with the bone stabilization device and forcing any bone filling material pas the connector and into the main body (e.g., into the cavity into which the stabilization device was inserted). In some variations, the device include a pressure-release mechanism, such as a channel, opening, bladder, etc. so that air (or excess bone filler) maybe bleed from the device or insertion site in a controlled way without contaminating the connector region. The handle and device may be configured as a pushable (e.g., plunger) device.

For example, described herein are methods of preparing the mating region of a bone stabilization implant for coupling with a secondary implant such as a bone screw that include the steps of: inserting a bone stabilization device into a bone, the bone stabilization device having a proximal connector; allowing the bone stabilization device to self-expand within the bone; injecting a bone filler in and around the bone stabilization device; and clearing bone filler from the connector region of the bone stabilization device using a clearing device, the clearing device comprising an elongate member having a proximal handle and a distal cleaning region.

The method may also include the step of attaching a secondary implant to the bone stabilization device; for example, screwing a bone screw into the connector region of the bone stabilization device.

The step of inserting the bone stabilization device may include inserting a bone stabilization device having a tubular elongate body and a plurality of self-expanding struts configured to extend therefrom. The step of allowing the bone stabilization device to self-expand comprises controlling the self-expansion of one or more struts of the bone stabilization device.

The step of injecting a bone filler in and around the bone stabilization device may comprise injecting a bone cement (e.g., PMMA, etc.) or any other appropriate filler. The bone filler may be allowed to set (e.g. harden) before of clearing bone filler from the connector region. This may prevent the device from being disturbed (e.g., moved) after it is implanted. The step of clearing bone filler from the connector region may include coupling the distal clearing region of the clearing device to the connector region of the bone stabilization device. For example, the clearing device may be screwed into a threaded connector region, or may engage the screws of a threaded connector region on the stabilization device. The step of clearing bone filler from the connector region may include scraping an edge region of the distal clearing region against the connector region. In some variations, the step of clearing bone filler from the connector region comprises applying suction to remove bone filler.

Also described are methods of cleaning a treaded connector of a bone stabilization implant so that it may mate with a secondary implant such as a bone screw. The method may include the steps of: inserting a bone stabilization implant into a bone, wherein the bone stabilization implant includes a threaded proximal region and a plurality of self-expanding struts; allowing the struts of the bone stabilization implant to self-expand within the bone; injecting a bone filler in and around the bone stabilization device; and clearing bone filler from the threaded proximal region of the bone stabilization device using a clearing device, the clearing device comprising an elongate member having a proximal handle and a distal clearing region configured to mate with the threaded proximal region of the bone stabilization implant.

Also described are kits for implanting a bone stabilization device and a secondary implant configured to couple to the bone stabilization device. For example, a kit may include a bone stabilization device and a clearing device. The bone stabilization device may be any of the devices described herein, including devices having a tubular elongate body and a plurality of self-expanding struts configured to extend therefrom, wherein the plurality of self-expanding struts are configured to cut through cancellous bone, a proximal connector region configured to connect to a secondary implant and a distal connector region configured to connect to the distal end of an inserter. The clearing device for clearing the proximal connector region of the self-expanding bone stabilization device may include: a proximal handle; an elongate shaft coupled to the proximal handle; and a distal cleaning region configured to mate with a proximal connector region of a bone stabilization device to remove bone filler from the proximal connector region. In some variations, the clearing device includes a vacuum port at the distal cleaning region.

The kits (which may also be systems) may also include bone filler (e.g., cement such as PMMA), and/or secondary implants such as bone screws, rods, cages, or the like.

BRIEF DESCRIPTION OF THE DRAWINGS

FIGS. 2D and 2E show a two-part bone screw, which may be configured as a pedicle screw.

FIG. 5A is a stabilization device to which a pedicle screw is attached.

FIG. 5B shows two implanted stabilization device and pedicle screws.

FIG. 5C is a stabilization device to which another variation of a pedicle screw is attached.

FIG. 6A is one variation of a stabilization device removably attached to an inserter.

FIGS. 7A-7J illustrate one method of treating a bone.

DETAILED DESCRIPTION OF THE INVENTION

Figure 1A:
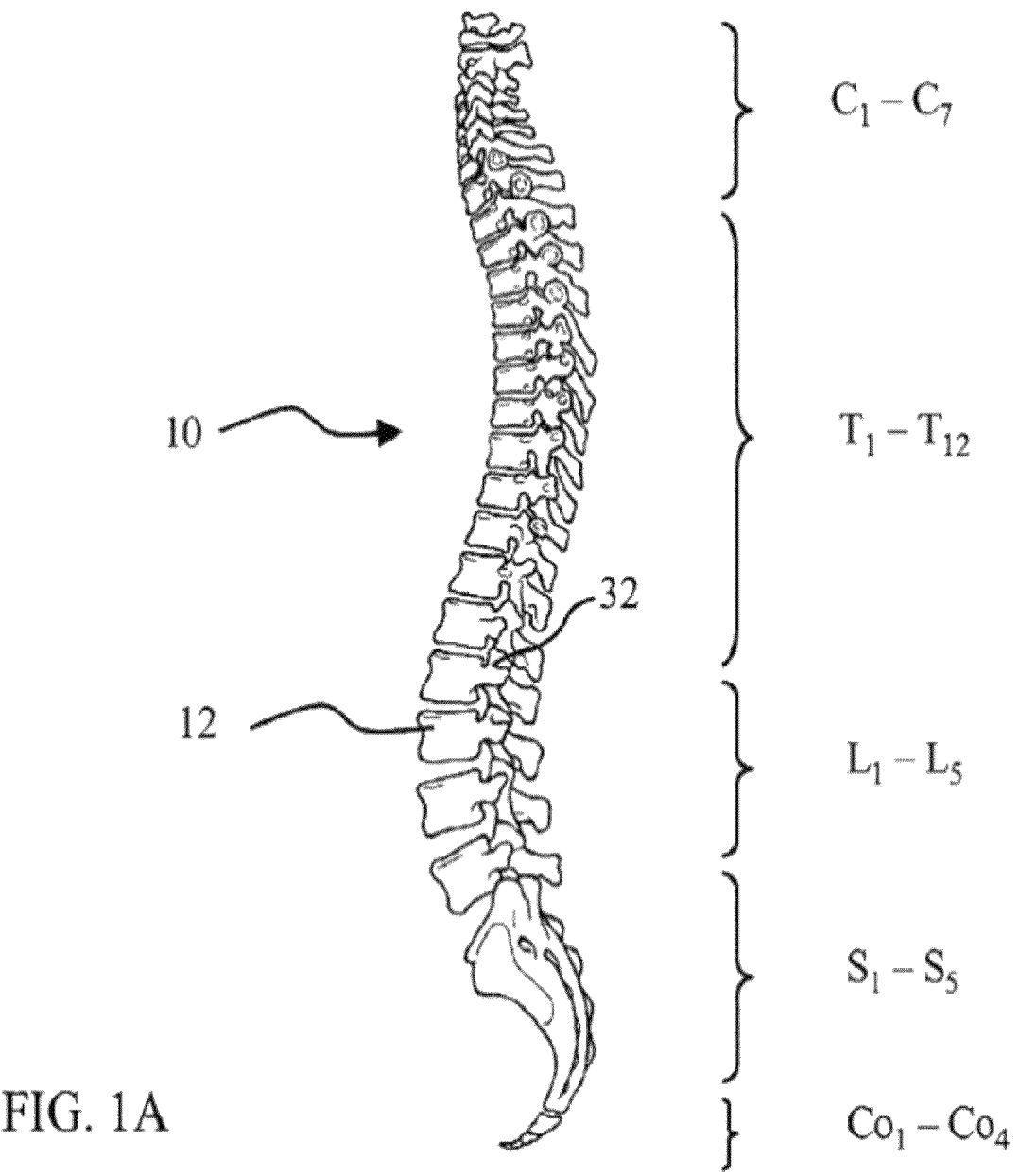
FIG. 1 is a lateral view of a normal human spinal column.
FIG. 1B is a superior view of a normal human lumbar vertebra.
FIG. 1C is a lateral view of a functional spinal unit having two vertebral bodies and an intervertebral disc.
FIG. 1D is a posterolateral oblique view of a vertebra.
FIG. 1E illustrates a portion of a spine wherein a vertebral body is fractured.
FIG. 1F illustrates a human body with the planes of the body identified.

The devices, systems and methods described herein may aid in the treatment of fractures and microarchitetcture deterioration of bone tissue, including vertebral compression fractures ("VCFs") or other indications including those arising from osteoporosis. The implantable stabilization devices described herein (which may be referred to as "stabilization devices" or simply "devices") may help restore and/or augment bone. Thus, the stabilization devices described herein may be used to treat pathologies or injuries. For purposes of illustration, many of the devices, systems and methods described herein are shown with reference to the spine. However, these devices, kits, systems and methods may be used in any appropriate body region, particularly bony regions. For example, the methods, devices and systems described herein may be used to treat hip bones.

Although examples of the use of the devices and methods described herein illustrate the use of these devices and methods to treat compression fractures, it should be understood that these methods and devices are not limited to treatment of compression fractures or to treatment of damage arising from osteoporosis. For example, the methods and device described herein may be used to treat bone damage arising from other disease states (e.g., cancer, tumors, infection, etc.) and non-disease states.

The devices described herein are may be referred to as "clearing devices" or "stabilization connector clearing devices" because they may be used to clear the connector regions of stabilization devices. One particular variation of a clearing device is a threaded bone filling material plunger ("threaded plunger").

In general a clearing device may include a handle, an elongate shaft (e.g., rod) and an end that is configured to mate with a connector region of a stabilization device. For example, the connector end may be threaded. In some variations, the device also includes a pressure release region. In some variations, the device are configured so that the connector region includes an absorbent material (e.g., sponge, fabric, etc.) for helping removing bone filler from the connecting region. In some variations, the distal end includes a solvent or other material to help selectively remove bone filler from the connector region.

The clearing devices described herein are to be used with self-expanding bone stabilization devices that may support one or more bone screws. Thus, a bone stabilization device may be inserted into a bone (e.g., a vertebral bone) and a bone screw may then be inserted into the stabilization device. In some variations the bone screw is inserted with the self-expanding stabilization device. In order to be used with the bone screw, the connector region of the bone stabilization device (the portion to which the bone screw attaches) must be relatively free of contamination from cement or the like. Thus, the clearing devices described herein may be used to clean or protect the connecting regions and prevent or remove contamination by bone filler.

Figure 7B:
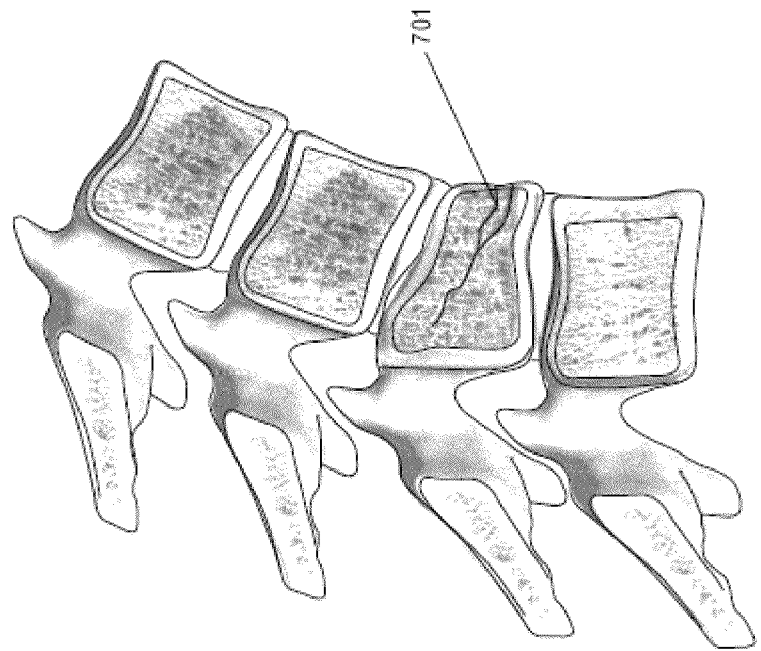
Figure 7A:
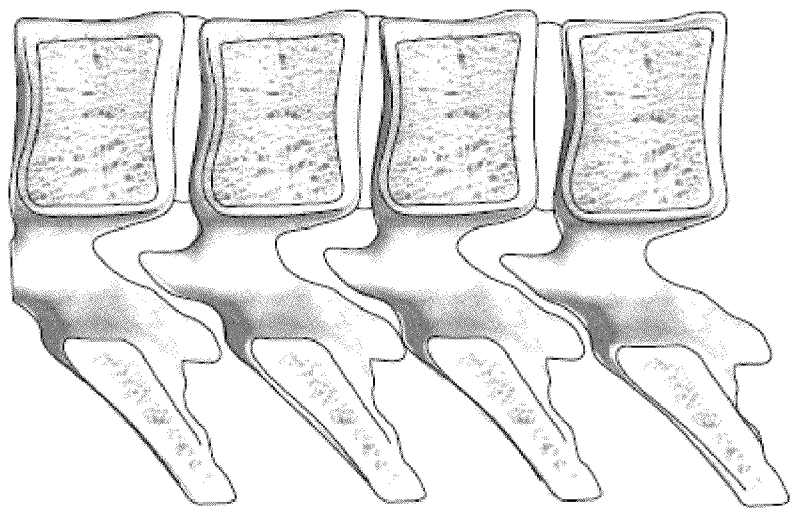

Described below in Section I is the background anatomy, including corresponding FIG. 1A-F. Section II, including FIGS. 2A-7J describes variations of stabilization devices having connector regions, and devices (e.g., bone screws, etc.) that may be connected to them via the connector regions. Section III illustrates one example of a clearing device (e.g., threaded bone filling material plunger). FIGS. 8 and 9 illustrate these devices and methods of using them.

By way of background the anatomy of the spine will briefly be described with reference to FIGS. 1A-1F, followed by a description of the bone stabilization devices (and variations of such devices) that may be used in any of these anatomical regions.

The human spinal column 10, as shown in FIG. 1A, is comprised of a series of thirty-three stacked vertebrae 12 divided into five regions. The cervical region includes seven vertebrae, known as C1-C7. The thoracic region includes twelve vertebrae, known as T1-T12. The lumbar region contains five vertebrae, known as L1-L5. The sacral region is comprised of five fused vertebrae, known as S1-S5, while the coccygeal region contains four fused vertebrae, known as Co1-Co4.

Figure 1B:
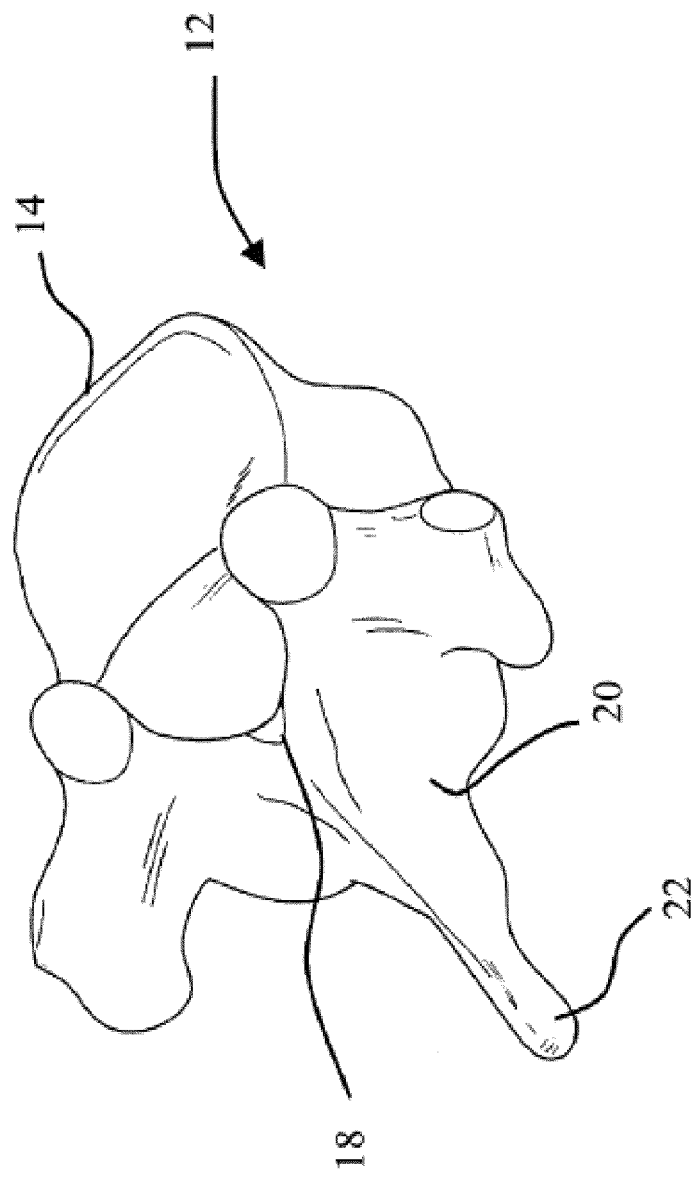
Figure 1C:
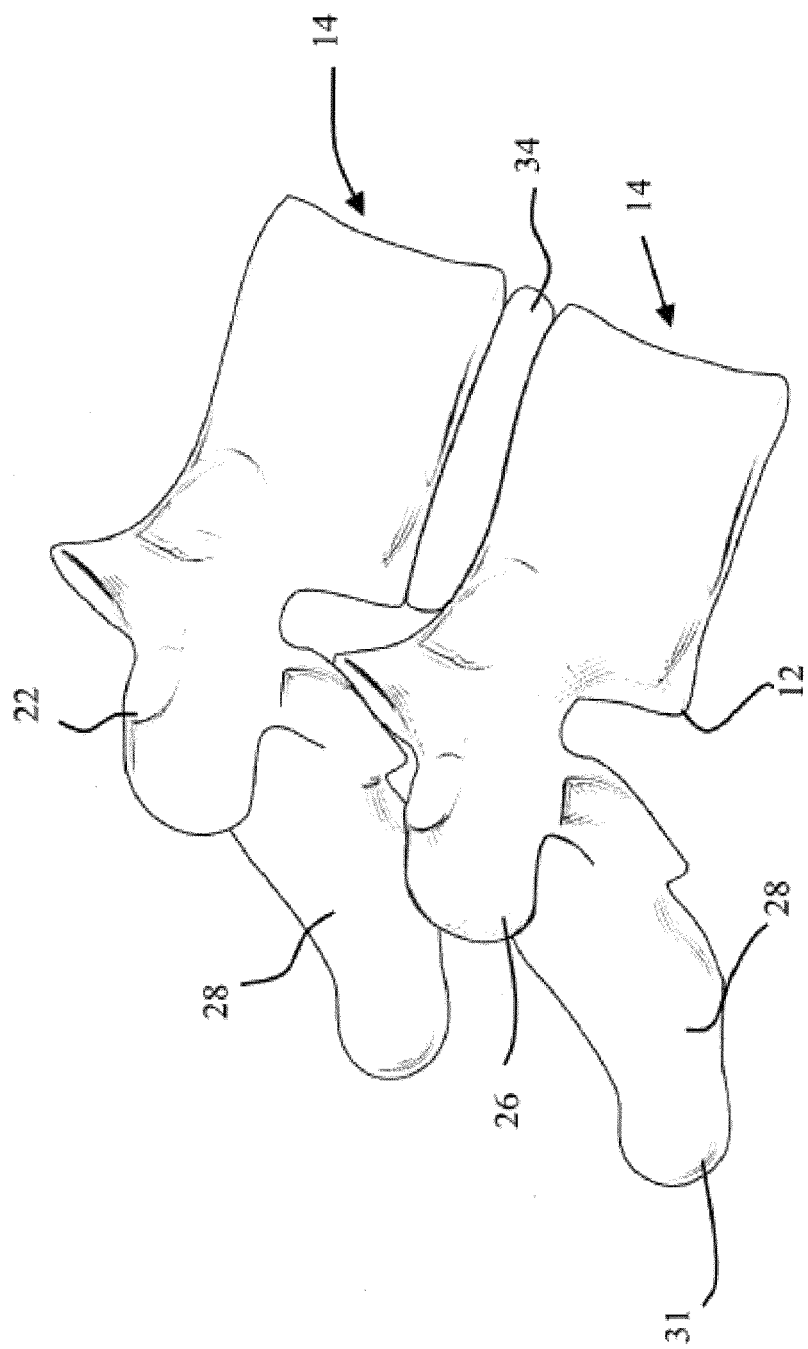

An example of one vertebra is illustrated in FIG. 1B, which depicts a superior plan view of a normal human lumbar vertebra 12. Although human lumbar vertebrae vary somewhat according to location, the vertebrae share many common features. Each vertebra 12 includes a vertebral body 14. Two short boney protrusions, the pedicles, extend dorsally from each side of the vertebral body 14 to form a vertebral arch 18 which defines the vertebral foramen.

At the posterior end of each pedicle, the vertebral arch 18 flares out into broad plates of bone known as the laminae 20. The laminae 20 fuse with each other to form a spinous process 22. The spinous process 22 provides for muscle and ligamentous attachment. A smooth transition from the pedicles to the laminae 20 is interrupted by the formation of a series of processes. Two transverse processes thrust out laterally, one on each side, from the junction of the pedicle with the lamina 20. The transverse processes serve as levers for the attachment of muscles to the vertebrae 12. Four articular processes, two superior and two inferior, also rise from the junctions of the pedicles and the laminae 20. The superior articular processes are sharp oval plates of bone rising upward on each side of the vertebrae, while the inferior processes 28, 28' are oval plates of bone that jut downward on each side.

The superior and inferior articular processes each have a natural bony structure known as a facet. The superior articular facet faces medially upward, while the inferior articular facet faces laterally downward. When adjacent vertebrae 12 are aligned, the facets, capped with a smooth articular cartilage and encapsulated by ligaments, interlock to form a facet joint 32. The facet joints are apophyseal joints that have a loose capsule and a synovial lining.

Figure 1D:
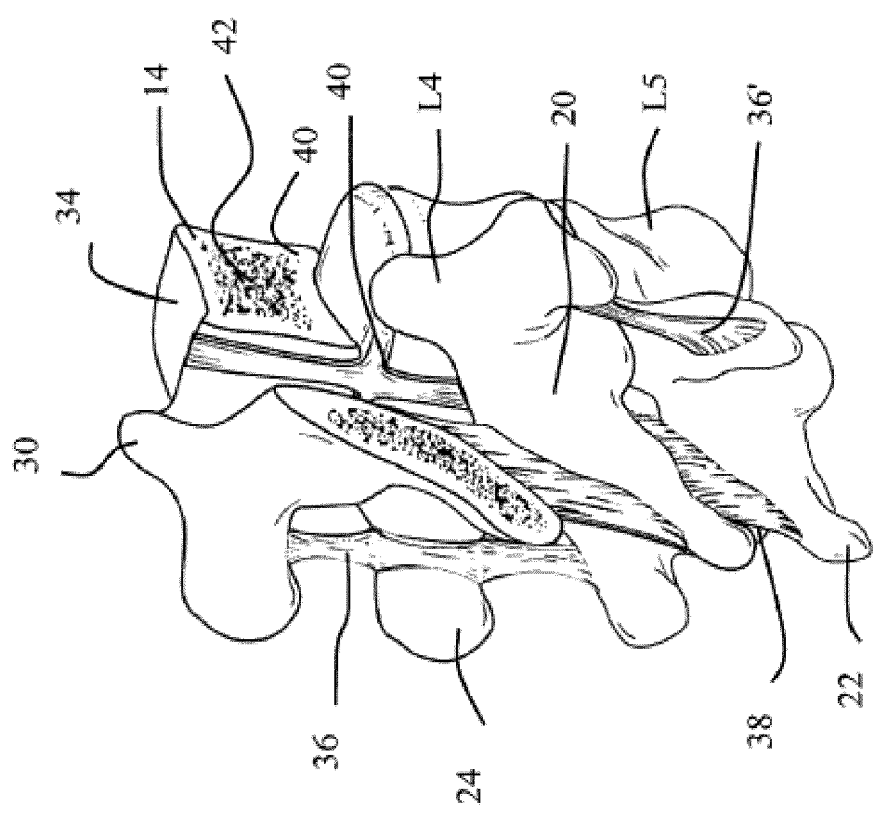

An intervertebral disc 34 between each adjacent vertebra 12 (with stacked vertebral bodies shown as 14, 15 in FIG. 1C) permits gliding movement between the vertebrae 12. The structure and alignment of the vertebrae 12 thus permit a range of movement of the vertebrae 12 relative to each other. FIG. 1D illustrates a posterolateral oblique view of a vertebra 12. The vertebral body 14 is shown in a cut-away that illustrates the cortical bone 40 which forms the exterior of the bone (in this case the vertebral body) and the spongy cancellous bone 42 located within the interior of the cortical bone.

Despite the small differences in mineralization, the chemical composition and true density of cancellous bone are similar to those of cortical bone. As a result, the classification of bone tissue as either cortical or cancellous is based on bone porosity, which is the proportion of the volume of bone occupied by non-mineralized tissue. Cortical bone has a porosity of approximately 5-30% whereas cancellous bone porosity may range from approximately 30 to more than 90%. Although typically cortical bone has a higher density than cancellous bone, that is not necessarily true in all cases. As a result, for example, the distinction between very porous cortical bone and very dense cancellous bone can be somewhat arbitrary.

The mechanical strength of cancellous bone is well known to depend on its apparent density and the mechanical properties have been described as those similar to man-made foams. Cancellous bone is ordinarily considered as a two-phase composite of bone marrow and hard tissue. The hard tissue is often described as being made of trabecular "plates and rods." Cancellous microstructure can be considered as a foam or cellular solid since the solid fraction of cancellous bone is often less than 20% of its total volume and the remainder of the tissue (marrow) is ordinarily not significantly load carrying. The experimental mechanical properties of trabecular tissue samples are similar to those of many man-made foams. If a sample of tissue is crushed under a prescribed displacement protocol, the load-displacement curve will initially be linear, followed by an abrupt nonlinear "collapse" where the load carrying capacity of the tissue is reduced by damage. Next follows a period of consolidation of the tissue where the load stays essentially constant, terminated by a rapid increase in the load as the tissue is compressed to the point where the void space is eliminated. Each of the mechanical properties of cancellous bone varies from site-to-site in the body. The apparent properties of cancellous bone as a structure depend upon the conformation of the holes and the mechanical properties of the underlying hard tissue composing the trabeculae. The experimental observation is that the mechanical properties of bone specimens are power functions of the solid volume fraction. The microstructural measures used to characterize cancellous bone are very highly correlated to the solid volume fraction. This suggests that the microstructure of the tissue is a single parameter function of solid volume fraction. If this is true, the hard tissue mechanical properties will play a large role in determining the apparent properties of the tissue. At this time, little is known about the dependence of trabecular hard tissue mechanical properties on biochemical composition or ultrastructural organization.

Cancellous bone in the joints and spine is continuously subject to significant loading. One consequence of this is that the tissue can experience, and occasionally accumulate, microscopic fractures and cracks. These small damages are similar to those seen in man-made materials and are, in many cases, the result of shear failure of the material. It is known that microcracks accumulate with age in the femoral head and neck, leading to a hypothesis that these damages are related to the increase in hip fracture with age. However, no such association of increased crack density with age was found in human vertebral cancellous bone despite the high incidence of spinal fractures, particularly in women.

Adult cortical and cancellous bone can be considered as a single material whose apparent density varies over a wide range. The compressive strength of bone tissue is proportional to the square of the apparent density. Cortical bone morphology and composition can be characterized by an examination of microstructure, porosity, mineralization, and bone matrix. These parameters seldom vary independently but are usually observed to vary simultaneously. Mechanical properties vary through the cortical thickness due to variations in microstructure, porosity, and chemical composition.

Mechanical properties are dependent on microstructure. The strongest bone type is circumferential lamellar bone, followed in descending order of strength by primary laminar, secondary Haversian, and woven-fibered bone. All normal adult cortical bone is lamellar bone. Most of the cortical thickness is composed of secondary Haversian bone. Circumferential lamellar bone is usually present at the endosteal and periosteal surfaces. In the adult, woven-fibered bone is formed only during rapid bone accretion, which accompanies conditions such as fracture callus formation, hyperparathyroidism, and Paget's disease.

Aging is associated with changes in bone microstructure which are caused primarily by internal remodeling throughout life. In the elderly, the bone tissue near the periosteal surface is stronger and stiffer than that near the endosteal surface due primarily to the porosity distribution through the cortical thickness caused by bone resorption. Bone collagen intermolecular cross-linking and mineralization increase markedly from birth to 17 years of age and continue to increase, gradually, throughout life. Adult cortical bone is stronger and stiffer and exhibits less deformation to failure than bone from children. Cortical bone strength and stiffness are greatest between 20 and 39 years of age. Further aging is associated with a decrease in strength, stiffness, deformation to failure, and energy absorption capacity.

Figure 1E:
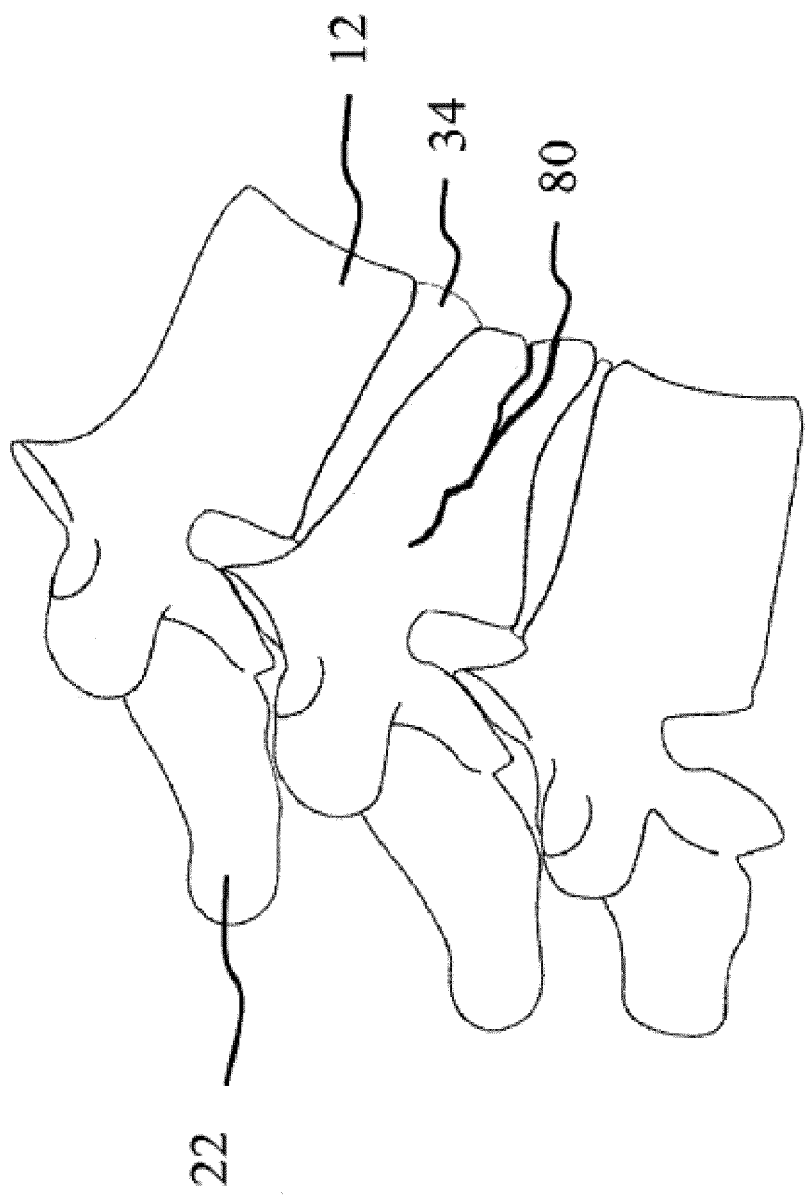
Figure 1F:
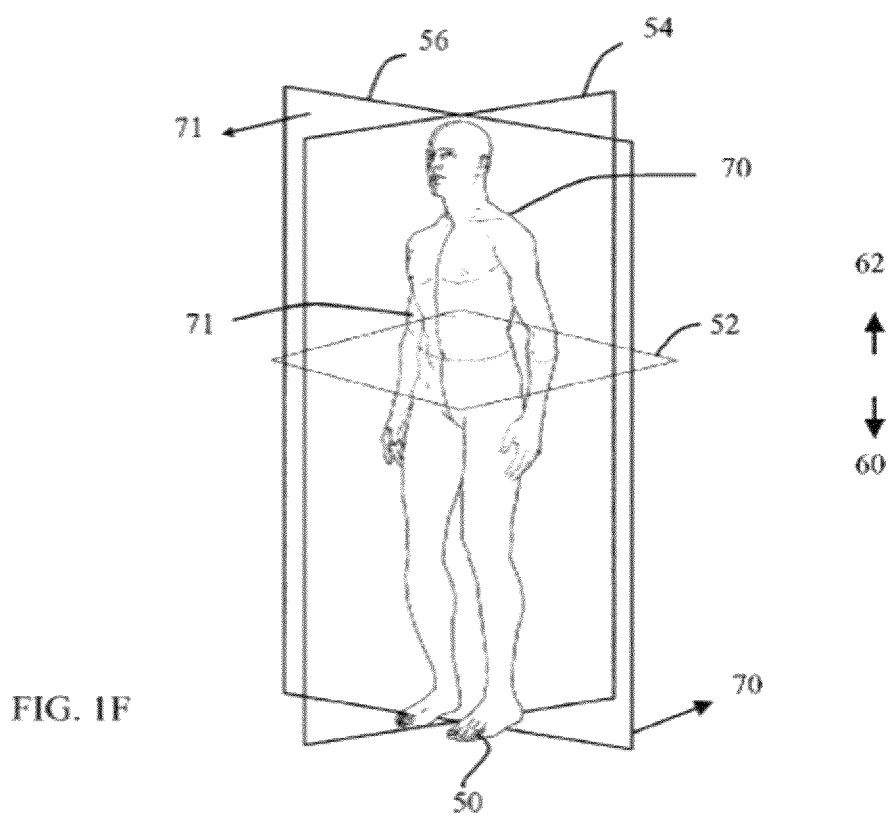

From this understanding of bone, it can be appreciated that when a vertebral body becomes damaged, as illustrated in FIG. 1E, such as when a fracture 80 occurs, a portion of the vertebral body typically collapses. This collapse can occur as a result of micro-architecture deterioration of the bone tissue.

The terms caudal and cephalad may be used in conjunction with the devices and operation of the devices and tools herein to assist in understanding the operation and/or position of the device and/or tools.

In order to understand the configurability, adaptability, and operational aspects of the devices disclosed herein, it is helpful to understand the anatomical references of the body 50 with respect to which the position and operation of the devices, and components thereof, are described. There are three anatomical planes generally used in anatomy to describe the human body and structure within the human body: the axial plane 52, the sagittal plane 54 and the coronal plane 56 (see FIG. 1F). Additionally, devices and the operation of devices and tools are better understood with respect to the caudad 60 direction and/or the cephalad direction 62. Devices and tools can be positioned dorsally 70 (or posteriorly) such that the placement or operation of the device is toward the back or rear of the body. Alternatively, devices can be positioned ventrally 72 (or anteriorly) such that the placement or operation of the device is toward the front of the body. Various embodiments of the devices, systems and tools of the present invention may be configurable and variable with respect to a single anatomical plane or with respect to two or more anatomical planes. For example, a component may be described as lying within and having adaptability or operability in relation to a single plane. For example, a device may be positioned in a desired location relative to an axial plane and may be moveable between a number of adaptable positions or within a range of positions. Similarly, the various components can incorporate differing sizes and/or shapes in order to accommodate differing patient sizes and/or anticipated loads.

The stabilization devices described herein may be self-expanding devices that expand from a compressed profile having a relatively narrow diameter (e.g., a delivery configuration) into an expanded profile (e.g., a deployed configuration). The stabilization devices generally include a shaft region having a plurality of struts that may extend from the shaft body. The distal and proximal regions of a stabilization device may include one or more attachment regions configured to attach to an inserter for inserting (and/or removing) the stabilization device from the body. The stabilization devices described herein may also include one or more bone screw attachment regions to which a bone screw (or screws) may be attached. In general, these devices may be used with any bone screw, including pedicle screws. FIGS. 2A-2E illustrate variations of pedicle screws that may be used with the devices described herein.

In general, inserting bone screws into the pedicles unaided takes a great deal of skill, as the dense bony parts of the pedicle are not large (e.g., pedicle thickness may be 4-6 mm), and a mistake could push a bone fragment into the spinal nerves, causing pain, loss of mobility and other damage, including damage to major blood vessels. To avoid this risk, the stabilization devices described herein may be used to position and secure screws, including pedicle screws, into the bone. The devices and method described herein may be used in conjunction with any appropriate visualization technique, including 3-D imaging, to place the stabilization devices into the bone, and then (or concurrently) place and position one or more screws through small incisions in the skin.

Figure 2A:
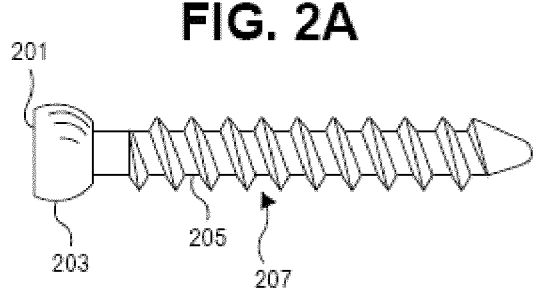
FIGS. 2A-2C are variations of pedicle screws.

In FIG. 2A, the pedicle screw 207 includes a head 203 that may be fixed or adjustable (e.g., rotatable), and may be keyed for use with a drill, screwdriver, or the like 201. A typical pedicle screw may also include a shaft region 205 that is threaded for insertion into the bone. The threads may be any size (e.g., minimum, maximum and pitch). In addition, the bone screw may be any appropriate length or thickness. In some variations, the bone screw has a thickness that is non-uniform along the length of the screw. Similarly, the threading may be non-uniform (e.g., may vary in pitch, maximum, minimum, etc.).

Figure 2B:
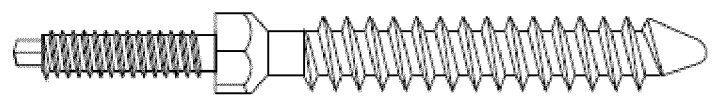

FIG. 2B shows another variation of a pedicle screw that includes a threaded front end, a head, and a threaded back end. This variation of a pedicle screw may be particularly useful in applying additional stabilization materials (e.g., plates, other screws, etc.). For example, in spinal fusion procedures.

Another variation of a one-piece pedicle screw has dual threads. For example, the screw may include a proximal region which has electrical threads (for attachment to the spine stabilization device) and the distal region has wood threads (e.g., in the outer portion that is configured to engage the pedicle). This screw can also be used with a cannula (e.g., canulated) and can have various lengths, pitch, and depths for each type of thread.

In some variations, the distal region of the screw (either a single-component screw of a multi-component screw) is conical, which may allow for ease of re-accessing a spine stabilization device or tissue region.

Figure 2C:
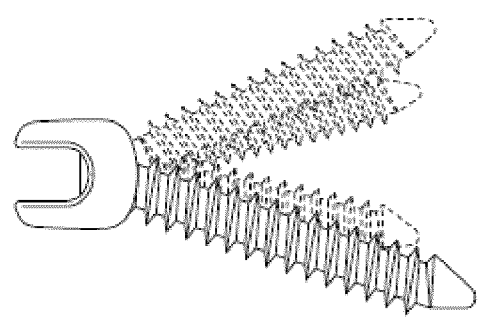

FIG. 2C is one variation of a polyaxial pedicle screw. This variation of a pedicle screw is threaded and the head is mobile (e.g., it swivels, helping to defray vertebral stress). Like other screws, polyaxial screws come in many sizes. For example, polyaxial pedicle screw length may vary from 30 mm to 60 mm (up to 2½ inches). The diameter may range from 5.0 mm to 8.5 mm (up to ¼ inch).

FIG. 2D shows both parts of a two-part bone screw that may be used. This variation of a pedicle screw includes a first bone screw assembly 210 that is configured to mate with the second bone screw assembly 212. In general, a two-part bone screw includes a first assembly that is configured to mate with the stabilization devices described herein, and a second bone screw assembly that is configured to secure to bone, and to mate with the first bone screw assembly. For example, the first bone screw assembly may be threaded 214 along the outer surface. The threads of the outer surface may engage a portion of the stabilization device (described in more detail below). The second bone screw assembly (or outer bone screw assembly) includes an inner region (e.g., threaded region) that engages the outer surface of the first bone screw assembly (not visible in FIG. 2D). In some variations this inner region extends at least partly through the length of the outer bone screw assembly. In other variations, the inner region extends completely through the outer bone screw assembly. The outer surface of the outer bone screw assembly is typically configured to engage bone. For example, the outer surface may be threaded 216, as shown in FIGS. 2D and 2E. In other variations, the outer surface includes other bone-engaging regions, such as protrusions, spurs, etc.

The proximal ends of either or both of the first and second bone screw assemblies of a two-part bone screw may be configured to engage a tool. For example, in FIG. 2D, the proximal end of the second bone screw assembly includes a head region 218. The head region may also be configured to engage an additional component, or it may be mobile, similar to FIG. 2C.

Different-sized first and second bone screw assemblies may be used to form the two-part bone screw. For example, a first bone screw assembly may be configured to mate with second bone screw assemblies having differ outer dimensions, threading pitches, threading heights, lengths, etc. This may allow customization of the two-part bone screw (and any system including them) to better fit a patient.

FIG. 2E illustrates the two-part bone screw of FIG. 2D in which the first and second assemblies are engaged with each other. In this example, the second bone screw assembly has been screwed onto the first bone screw assembly so that the proximal end of the first bone screw assembly extends past the proximal end of the second bone screw assembly.

The distal ends of either (or both) the first and second bone screw assemblies may be configured in any appropriate manner. For example, the distal end of the first bone screw assembly may be configured as a point or taper, as rounded, or as flat. The distal end of the second bone screw assembly is typically configured as opened to mate with the first bone-screw assembly, but this region may also be configured as tapered, smooth, or the like. For example the bone-engaging outer surface (e.g., threads 316) may begin proximal to the distal end, and may increase in size (e.g., depth) along the proximal end of the second bone screw assembly.

The pitch and size of the outer threading of the second bone screw assembly 216 in FIGS. 2D and 2E is generally greater than the pitch and size of the outer threading of the first bone screw assembly. In some variations, the pitch and/or size of these threading is the same, or the pitch and/or size of the outer threading on the first (inner) bone screw assembly is greater than the pitch and/or size of the outer threading on the second (outer) bone screw assembly. It may be particularly advantageous to have a larger pitch and/or larger size threading on the outer bone screw assembly, since it is typically configured to engage bone. The first and second bone screw assemblies may be formed of any appropriate material, including those used for the screws in FIGS. 2A-2C. Appropriately durable biocompatible materials (such as stainless steel) may be particularly appropriate. Coatings (e.g., low-friction coatings, drug coatings, etc.) may also be used. The materials forming the first and second bone screw assemblies may be the same, or they may be different.

In some variations for inserting a multi-part screw and a bone stabilization device, the outer component of the screw may be positioned before the inner component, and then the inner (smaller-diameter) component may be positioned and secured. For example, the multi-part screw may be attached by placing the outer screw first (after placement of the spine stabilizing device) over a pin wire (e.g., guidewire) or over the delivery device used to for the spine stabilization device, and then placing and securing the inter-screw.

The pedicle screws described herein may be any appropriate dimensions and may be made of any appropriate material. For example, the screws may be Titanium, which is highly resistant to corrosion and fatigue, and is MRI compatible.

Figure 3A:
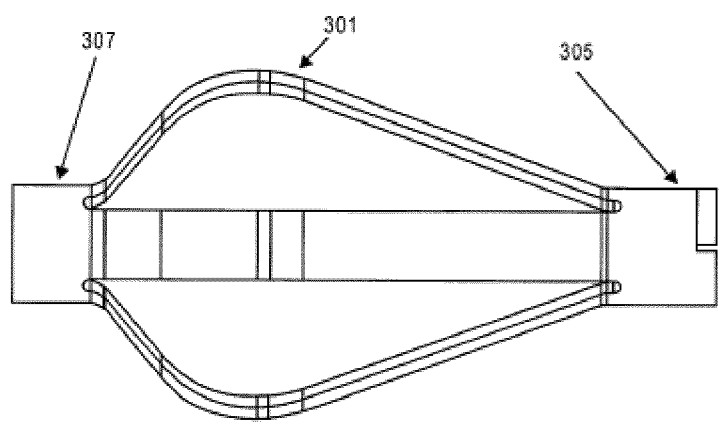
FIGS. 3A and 3B are enlarged side and side perspective views (respectively) of a stabilization device.

FIGS. 3A through 4B show exemplary stabilization devices that may be used with bone screws as described herein. Side profile views of one variation of a stabilization device are shown in FIGS. 3A and 3B. FIGS. 3A and 3B show a 10 mm asymmetric stabilization device in an expanded configuration. The device has four struts 301 formed by cutting four slots down the length of the shaft. In this example, the elongate expandable shaft has a hollow central lumen, and a proximal end 305 and a distal end 307. By convention, the proximal end is the end closest to the person inserting the device into a subject, and the distal end is the end furthest away from the person inserting the device.

The struts 301 of the elongate shaft is the section of the shaft that projects from the axial (center) of the shaft. Three struts are visible in each of FIGS. 3A and 3B. In general, each strut has a leading exterior surface that forms a cutting surface adapted to cut through cancellous bone as the strut is expanded away from the body of the elongate shaft. This cutting surface may be shaped to help cut through the cancellous bone (e.g., it may have a tapered region, or be sharp, rounded, etc.)). In some variations, the cutting surface is substantially flat.

Figure 3B:
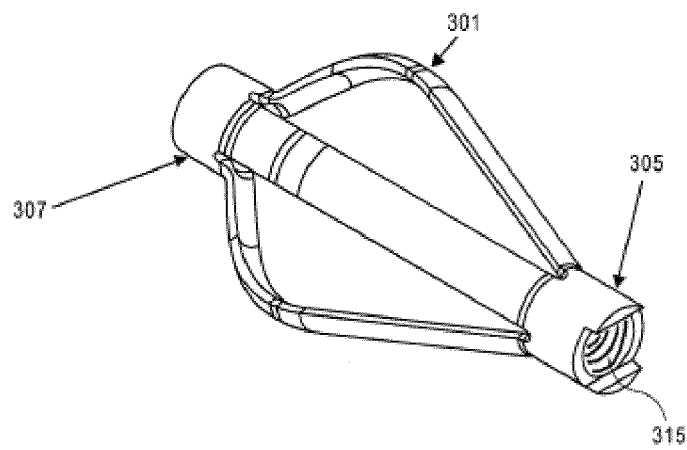

The stabilization device is typically biased so that it is relaxed in the expanded or deployed configuration, as shown in FIGS. 3A and 3B. In general, force may be applied to the stabilization device so that it assumes the narrower delivery profile. Thus, the struts may elastically bend or flex from the extended configuration to the unextended configuration.

The struts in these examples are continuous curvature of bending struts. Continuous curvature of bending struts are struts that do not bend from the extended to an unextended configuration (closer to the central axis of the device shaft) at a localized point along the length of the shaft. Instead, the continuous curvature of bending struts are configured so that they translate between a delivery and a deployed configuration by bending over the length of the strut rather than bending at a discrete portion (e.g., at a notch, hinge, channel, or the like). Bending typically occurs continuously over the length of the strut (e.g., continuously over the entire length of the strut, continuously over the majority of the length of the strut (e.g., between 100-90%, 100-80%, 100-70%, etc.), continuously over approximately half the length of the strut (e.g., between about 60-40%, approximately 50%, etc.). In some variations of the self-expanding devices described herein, the struts do not have a continuous curvature of bending, but may be bent or hinged, or may include one or more notches along the length of the strut to facilitate bending.

The "curvature of bending" referred to by the continuous curvature of bending strut is the curvature of the change in configuration between the delivery and the deployed configuration. The actual curvature along the length of a continuous curvature of bending strut may vary (and may even have "sharp" changes in curvature). However, the change in the curvature of the strut between the delivery and the deployed configuration is continuous over a length of the strut, as described above, rather than transitioning at a hinge point. Struts that transition between delivery and deployed configurations in such a continuous manner may be stronger than hinged or notched struts, which may present a pivot point or localized region where more prone to structural failure.

A continuous curvature of bending strut typically does not include one or more notches or hinges along the length of the strut. Two variations of continuous curvature of bending struts are notchless struts and/or hingeless struts. In FIG. 3A, the strut 301 bends in a curve that is closer to the distal end of the device than the proximal end (making this an asymmetric device). In this example, the maximum distance between the struts along the length of device is approximately 10 mm in the relaxed (expanded) state. Thus, this may be referred to as a 10 mm asymmetric device.

The device shown in FIGS. 3A and 3B also include one or more bone screw attachment region(s). For example, in FIG. 3A the bone screw attachment region is located at the proximal 305 end of the shaft. As described in more detail below, this proximal end may also be adapted to releasably engage an inserter for inserting the stabilization device into the bone.

In general a bone screw attachment site is configured to secure a bone screw to the device and therefore into the bone. For example, a bone screw attachment region or site may include an opening or passage into which the bone screw may be inserted. In some variations the bone screw attachment passage is threaded in a manner that is complementary to the bone screw that may be inserted into the device. Thus, in some variations, the bone screw attachment site is configured to mate with a particular size or shape of bone screw (e.g., the size and pitch of threads). In some variations, the bone screw attachment region comprises a passageway that is not threaded, but is configured to be compressed by the bone screw as it is inserted. For example, the bone screw attachment region may include a crushable material (e.g., a porous, frangible, or compressible material) that the bone screw may crush when inserted therethrough.

In some variations, the bone screw attachment region is an opening through which the bone screw may pass, so that the self-expanding stabilization device guides the bone screw insertion. In some variations an adapter or sleeve may be inserted in (or may be present within) the bone screw attachment region of the device. The bone screw may be inserted into the sleeve or adapter. This may allow one size of bone screw attachment region to be used with a variety of differently sized bone screws.

In some variations, the bone screw attachment region is a post or projection connected to or integral with the stabilization device onto which the bone screw (or a portion or component of a bone screw) mates. For example, a bone screw attachment region may be a post projecting from an outer (or inner) surface of the stabilization device over which a bone screw coaxially slides.

The proximal end (the end facing to the right in FIGS. 3A and 3B), shows one variation of an attachment region to which the device may be attached to one portion of an introducer. As mentioned above, this same end of the device may include a bone screw attachment region. The devices shown in FIG. 3A-4B include a bone screw attachment region that passes through this proximal end and into the lumen of the elongate shaft.

In FIG. 3B, the proximal end 305 also includes a cut-out region, forming a seating area into which a complementary attachment region or connector region of an inserter may mate. In some variations, this notch (or cut-out region) is not present. In this example, the bone screw attachment region is a threaded region 315 that is visible within the lumen of the shaft. The attachment regions are also referred to as connector regions. These threads may be used to secure to a bone screw, and/or to releasably secure to an inserter. Thus, the distal region 307 of the device may include an attachment region for attaching the device to an inserter. Alternative or additional bone screw attachment regions may also be included. For example, the distal end of the device may also include a bone screw attachment region.

In addition to the bone screw attachment region(s), the devices described herein may also include an attachment region for releasably attaching to an inserter. To distinguish the inserter attachment regions from the bone screw attachment regions, bone screw attachment regions may be referred to as "bone screw attachment regions" and inserter attachment regions may be referred to as "inserter attachment regions" or simply as "attachment regions", although in some variations it should be clear that the same regions of the device may be both bone screw attachment regions and inserter attachment regions.

An inserter attachment region may be configured in any appropriate way. For example, the attachment region may be a cut-out region (or notched region), including an L-shaped cut out, an S-shaped cut out, a J-shaped cut out, or the like, into which a pin, bar, or other structure on the inserter may mate. In some variations, the attachment region is a threaded region which may mate with a pin, thread, screw or the like on the inserter. As mentioned, these same regions may also be bone screw attachment regions. In some variations, the inserter attachment region is a hook or latch. The attachment region may be a hole or pit, with which a pin, knob, or other structure on the inserter mates. In some variations, the attachment region includes a magnetic or electromagnetic attachment (or a magnetically permeable material), which may mate with a complementary magnetic or electromagnet region on the inserter. In each of these variations the attachment region on the device mates with an attachment region on the inserter so that the device may be removably attached to the inserter.

The stabilization devices described herein generally have two or more releasable inserter attachment regions for attaching to an inserter. For example, a stabilization device may include at least one inserter attachment region at the proximal end of the device and another inserter attachment region at the distal end of the device. This may allow the inserter to apply force across the device (e.g., to pull the device from the expanded deployed configuration into the narrower delivery configuration), as well as to hold the device at the distal end of the inserter. However, the stabilization devices may also have a single attachment region (e.g., at the proximal end of the device). In this variation, the more distal end of the device may include a seating region against which a portion of the inserter can press to apply force to change the configuration of the device. In some variations of the self-expanding stabilization devices, the force to alter the configuration of the device from the delivery to the deployed configuration comes from the material of the device itself (e.g., from a shape-memory material), and thus only a single attachment region (or one or more attachment region at a single end of the device) is necessary.

Figure 4A:
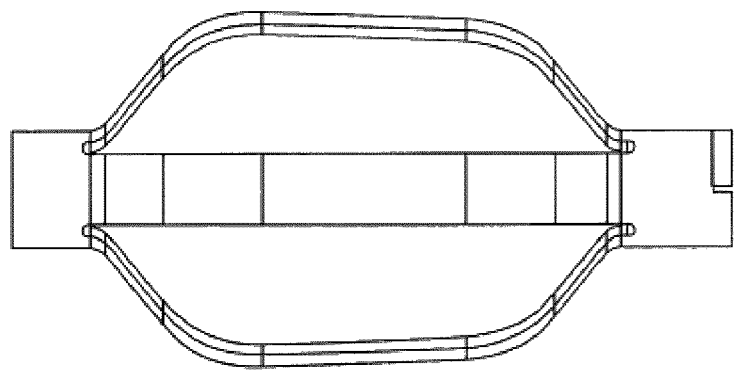
FIGS. 4A and 4B are enlarged side and side perspective views (respectively) of a stabilization device.
Figure 4B:
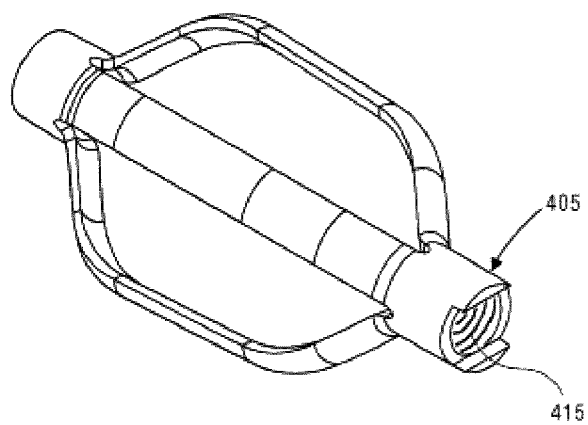

FIGS. 4A and 4B show side and side perspective views of exemplary symmetric 10 mm devices. In FIG. 4B the bone screw attachment region (shown in FIG. 4B as a threaded region 415) is located within the proximal 405 end of the device.

The struts described herein (including the continuous curvature of bending struts) may be any appropriate dimension (e.g., thickness, length, width), and may have a uniform cross-sectional thickness along their length, or they may have a variable cross-sectional thickness along their length. For example, the region of the strut that is furthest from the tubular body of the device when deployed (e.g., the curved region 301 in FIGS. 3A and 3B) may be wider than other regions of the strut, providing an enhanced contacting surface that abuts the non-cancellous bone after deployment.

The dimensions of the struts may also be adjusted to calibrate or enhance the strength of the device, and/or the force that the device exerts to self-expand. For example, thicker struts (e.g., thicker cross-sectional area) may exert more force when self-expanding than thinner struts. This force may also be related to the material properties of the struts.

The struts may be made of any appropriate material. In some variations, the struts and other body regions are made of substantially the same material. Different portions of the stabilization device (including the struts) may be made of different materials. In some variations, the struts may be made of different materials (e.g., they may be formed of layers, and/or of adjacent regions of different materials, have different material properties). The struts may be formed of a biocompatible material or materials. It may be beneficial to form struts of a material having a sufficient spring constant so that the device may be elastically deformed from the deployed configuration into the delivery configuration, allowing the device to self-expand back to approximately the same deployed configuration. In some variation, the strut is formed of a shape memory material that may be reversibly and predictably converted between the deployed and delivery configurations. Thus, a list of exemplary materials may include (but is not limited to): biocompatible metals, biocompatible polymers, polymers, and other materials known in the orthopedic arts. Biocompatible metals may include cobalt chromium steel, surgical steel, titanium, titanium alloys (such as the nickel titanium alloy Nitinol™), tantalum, tantalum alloys, aluminum, etc. Any appropriate shape memory material, including shape memory alloys such as Nitinol™ may also be used.

Other regions of the stabilization device may be made of the same material(s) as the struts, or they may be made of a different material. Any appropriate material (preferably a biocompatible material) may be used (including any of those materials previously mentioned), such as metals, plastics, ceramics, or combinations thereof. In variations where the devices have bearing surfaces (i.e. surfaces that contact another surface), the surfaces may be reinforced. For example, the surfaces may include a biocompatible metal. Ceramics may include pyrolytic carbon, and other suitable biocompatible materials known in the art. Portions of the device can also be formed from suitable polymers include polyesters, aromatic esters such as polyalkylene terephthalates, polyamides, polyalkenes, poly(vinyl) fluoride, PTFE, polyarylethyl ketone, and other materials. Various alternative embodiments of the devices and/or components could comprise a flexible polymer section (such as a biocompatible polymer) that is rigidly or semi rigidly fixed.

For example, the bone screw attachment region may be made of any appropriate material. A bone screw attachment region may include a coating or layer. In particular, materials that help secure the bone screw within the stabilization device or ease the insertion of the bone screw into the device may be used. For example, the bone screw attachment region may include a coating of a friction-reducing material, or a friction-enhancing material. As mentioned above, the bone screw attachment region may include a layer of compressible or crushable material. In some variations the bone screw attachment region comprises a channel for the insertion of a bone screw that is formed of a relatively uncompressible material (e.g., a metal such as steel or titanium) surrounding a relatively compressible material (e.g., aluminum, tin, porous materials, rubbers, frangible materials, etc).

Thus the devices (including the struts), may also include one or more coating or other surface treatment (embedding, etc.). Coatings may be protective coatings (e.g., of a biocompatible material such as a metal, plastic, ceramic, or the like), or they may be a bioactive coating (e.g., a drug, hormone, enzyme, or the like), or a combination thereof. For example, the stabilization devices may elute a bioactive substance to promote or inhibit bone growth, vascularization, etc. In one variation, the device includes an elutible reservoir of bone morphogenic protein (BMP).

As previously mentioned, the stabilization devices may be formed about a central elongate hollow body. In some variations, the struts are formed by cutting a plurality of slits long the length (distal to proximal) of the elongate body. This construction may provide one method of fabricating these devices, however the stabilization devices are not limited to this construction. If formed in this fashion, the slits may be cut (e.g., by drilling, laser cutting, etc.) and the struts formed by setting the device into the deployed shape so that this configuration is the default, or relaxed, configuration in the body. For example, the struts may be formed by plastically deforming the material of the struts into the deployed configuration. In general, any of the stabilization devices may be thermally treated (e.g., annealed) so that they retain this deployed configuration when relaxed. Thermal treatment may be particularly helpful when forming a strut from a shape memory material such as a nickel-titanium alloy (e.g., Nitinol™) into the deployed configuration.

FIG. 5A shows one variation of a stabilization device 501 including a bone screw attachment region. A bone screw 503 is shown attached to the stabilization device 501. In this example, the bone screw attachment region is located at the proximal end of the device. The device 501 includes a hollow body into which the bone screw may be inserted. In use, the bone screw may be inserted into the device either before, during, or after the device has been inserted into the subject's bone.

FIG. 5B illustrates two stabilization devices 511, 511' inserted into a spinal segment. A pedicle (bone) screw 513, 513' has been inserted into each stabilization device. In some variations, the distal end of the device may also include a bone screw attachment region, so that a pedicle screw may be stabilized both at the proximal and the distal ends of the device. Thus, a bone screw may be inserted completely through the stabilization device, and may extend from the distal end. In some variations, the central region of the device includes a continuous (or mostly continuous) channel into which the bone screw may pass.

FIG. 5C shows another variation of a system including a stabilization device 501 having a bone screw attachment region and a bone screw 523. The bone screw in this example is a two-part bone screw 523 in which the first bone screw assembly 525 attaches to the stabilization device 501, and the second bone screw assembly 527 attaches to the first bone screw assembly. In some variations, the second bone screw assembly may also attach to the stabilization device 501. In use, the first and second bone screw assemblies may be inserted into the device, and/or may engage with each other either before, during, or after the device has been inserted into the subject's bone.

Any of the stabilization device described herein may be used with an inserter that may position the self-expanding stabilization device within the subject's bone. FIG. 6A shows one variation of a stabilization device 600 having a plurality of continuous curvature of bending struts 601, 601' removably attached to an inserter 611. This stabilization device also includes at least one bone screw attachment device. In this example, an inserter attachment region 615 at the proximal portion of the stabilization device is configured as an L-shaped notch, as is the attachment region 613 at the distal portion of the device.

In general, an inserter includes an elongate body having a distal end to which the stabilization device may be attached and a proximal end which may include a handle or other manipulator that coordinates converting an attached stabilization device from a delivery and a deployed configuration, and also allows a user to selectively release the stabilization device from the distal end of the inserter.

The inserter 611 shown in FIG. 6A includes a first elongate member 621 that coaxially surrounds a second elongate member 623. In this variation, each elongate member 621, 623 includes a stabilization device attachment region at its distal end, to which the stabilization device is attached, as shown. In this example, the stabilization device attachment region includes a pin that mates with the L-shaped slots forming the releasable attachment regions on the stabilization device. In FIG. 6A the L-shaped releasable attachments on the stabilization device are oriented in opposite directions (e.g., the foot of each "L" points in opposite directions). Thus, the releasable attachment devices may be locked in position regardless of torque applied to the inserter, preventing the stabilization device from being accidentally disengaged.

The inserter shown in FIG. 6A also includes two grips 631, 633 at the proximal ends of each elongate member 621, 623. These grips can be used to move the elongate members (the first 621 or second 623 elongate member) relative to each other. The first and second elongate members of the inserter may be moved axially (e.g., may be slid along the long axis of the inserter) relative to each other, and/or they may be moved in rotation relative to each other (around the common longitudinal axis). Thus, when a stabilization device is attached to the distal end of the inserter, moving the first elongate member 621 axially with respect to the second elongate member 623 will cause the stabilization device to move between the deployed configuration (in which the struts are expanded) and the delivery configuration (in which the struts are relatively unexpanded). Furthermore, rotation of the first elongate member of the inserter relative to the second elongate member may also be used to disengage one or more releasable attachment regions of the stabilization device 613, 615 from the complementary attachment regions of the inserter 625, 627. Although he stabilization devices described herein are typically self-expanding stabilization devices, devices that do not self-expand may be used (especially devices having a bone screw attachment region). Even in self-expanding devices, the inserter may be used to apply additional force to convert the stabilization device between the delivery and the deployed configuration. For example, when allowed to expand in a cancellous bone, the force applied by the struts when self-expanding may not be sufficient to completely cut through the cancellous bone and/or distract the cortical bone as desired. In some variations, the inserter may also permit the application of force to the stabilization device to expand the struts even beyond the deployed configuration.

Figure 6B:
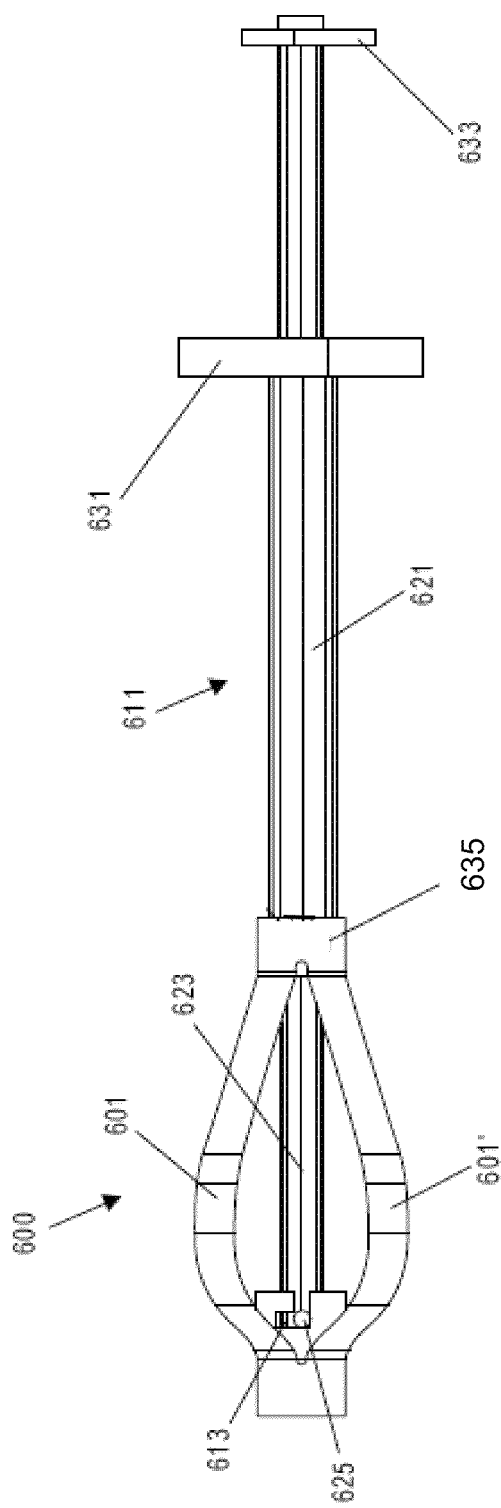
FIG. 6B is another variation of a stabilization device removably attached to an inserter.

FIG. 6B is another variation of a stabilization device 600 releasably connected to an inserter 611, in which the attachment region 635 between the stabilization device and the inserter is configured as a screw or other engagement region, rather than the notch 615 shown in FIG. 6A.

An inserter may also limit or guide the movement of the first and second elongate members, so as to further control the configuration and activation of the stabilization device. For example, the inserter may include a guide for limiting the motion of the first and second elongate members. A guide may be a track in either (or both) elongate member in which a region of the other elongate member may move. The inserter may also include one or more stops for limiting the motion of the first and second elongate members.

As mentioned above, the attachment regions on the inserter mate with the stabilization device inserter attachments. Thus, the attachment regions of the inserter may be complementary attachments that are configured to mate with the stabilization device inserter attachments. For example, a complimentary attachment on an inserter may be a pin, knob, or protrusion that mates with a slot, hole, indentation, or the like on the stabilization device. In some variations the attachment region is a threaded region. The complementary attachment (the attachment region) of the inserter may be retractable. For example, the inserter may include a button, slider, etc. to retract the complementary attachment so that it disconnects from the stabilization device attachment. A single control may be used to engage/disengage all of the complementary attachments on an inserter, or they may be controlled individually or in groups.

In some variation the inserter includes a lock or locks that hold the stabilization device in a desired configuration. For example, the inserter may be locked so that the stabilization device is held in the delivery configuration (e.g., by applying force between the distal and proximal ends of the stabilization device). In an inserter such as the one shown in FIG. 6A, for example, a lock may secure the first elongate member to the second elongate member so that they may not move axially relative to each other.

In some variations, the inserter includes a space or passage for a bone screw that may be pre-attached to the stabilization device before the device is implanted. The inserter may also include a holder (or holding region) for a bone screw, and the inserter may be used to attach the bone screw to a stabilization device after it has been implanted.

Any of the inserters described herein may include, or may be used with, a handle. A handle may allow a user to control and manipulate an inserter. For example, a handle may conform to a subject's hand, and may include other controls, such as triggers or the like. Thus, a handle may be used to control the relative motion of the first and second elongate members of the inserter, or to release the connection between the stabilization device and the inserter, or any of the other features of the inserter described herein.

An inserter may be packaged or otherwise provided with a stabilization device attached. Thus, the inserter and stabilization device may be packaged sterile, or may be sterilizable. In some variations, a reusable handle is provided that may be used with a pre-packaged inserter stabilization device assembly.

Any of the stabilization device including bone screw attachment sites may also be included with a bone screw or screws. Thus a system or kit including a stabilization device may also include one or more bone screws.

As mentioned above, in the delivery configuration the struts of the stabilization device are typically closer to the long axis of the body of the stabilization device. Thus, the device may be inserted into the body for delivery into a bone region. This may be accomplished with the help of an access cannula (which may also be referred to as an introducer). Any of the devices (stabilization devices) and inserters (including handles) may be included as part of a system or kit for correcting a bone defect or injury. A trocar may also be used with an access cannula to insert the devices. Any appropriate length cannula and trocar may be used, so long as it is correctly scaled for use with the introducer and stabilization device. A trocar and an introducer may be used to cut through tissue until reaching bone, so that the introducer can be positioned appropriately.

A bone drill may be used to access the cancellous bone to insert any of the devices described. A twist drill may be used with the same access cannula previously described. The distal (drill) end of the twist drill may extend from the cannula, and be used to drill into the bone.

Any of the devices shown and described herein may also be used with a bone cement. For example, a bone cement may be applied after inserting the stabilization device into the bone, before or after attaching a bone screw. Bone cement may be used to provide long-term support for the repaired bone region and bone screw. Any appropriate bone cement or filler may be used, including PMMA, bone filler or allograft material. Suitable bone filler material include bone material derived from demineralized allogenic or xenogenic bone, and can contain additional substances, including active substance such as bone morphogenic protein (which induce bone regeneration at a defect site). Thus materials suitable for use as synthetic, non-biologic or biologic material may be used in conjunction with the devices described herein, and may be part of a system includes these devices. For example, polymers, cement (including cements which comprise in their main phase of microcrystalline magnesium ammonium phosphate, biologically degradable cement, calcium phosphate cements, and any material that is suitable for application in tooth cements) may be used as bone replacement, as bone filler, as bone cement or as bone adhesive with these devices or systems. Also included are calcium phosphate cements based on hydroxylapatite (HA) and calcium phosphate cements based on deficient calcium hydroxylapatites (CDHA, calcium deficient hydroxylapatites). See, e.g., U.S. Pat. No. 5,405,390 to O'Leary et al.; U.S. Pat. No. 5,314,476 to Prewett et al.; U.S. Pat. No. 5,284,655 to Bogdansky et al.; U.S. Pat. No. 5,510,396 to Prewett et al.; U.S. Pat. No. 4,394,370 to Jeffries; and U.S. Pat. No. 4,472,840 to Jeffries, which describe compositions containing demineralized bone powder. See also U.S. Pat. No. 6,340,477 to Anderson which describes a bone matrix composition. Each of these references is herein incorporated in their entirely.

Exemplary Method of Repairing a Bone

As mentioned above, any of the devices described herein may be used to repair a bone. A method of treating a bone using the devices describe herein typically involves delivering a stabilization device (e.g., a self-expanding stabilization device as described herein including a bone screw attachment region) within a cancellous bone region, and allowing the device to expand within the cancellous bone region so that a cutting surface of the device cuts through the cancellous bone.

For example, the stabilization devices described herein may be used to repair a compression fracture in spinal bone. This is illustrated schematically in FIGS. 7A-7J. FIG. 7A shows a normal thoracic region of the spine in cross-section along the sagital plane. The spinal vertebras are aligned, distributing pressure across each vertebra. FIG. 7B shows a similar cross-section through the spine in which there is a compression fracture in the $11^{th}$ thoracic vertebra 701. The $11^{th}$ vertebra is compressed in the fractured region. It would be beneficial to restore the fractured vertebra to its uninjured position, by expanding (also referred to as distracting) the vertebra so that the shape of the cortical bone is restored. It may also be useful to insert a pedicle (bone) screw so that this spinal region can be fused. This may be achieved by inserting and expanding one of the stabilization devices described herein, and then attaching a pedicle screw. In order to insert the stabilization device, the damaged region of bone must be accessed.

As mentioned above, an introducer (or access cannula) and a trocar may be used to insert the access cannula adjacent to the damaged bone region. Any of the steps described herein may be aided by the use of an appropriate visualization technique. For example, a fluoroscope may be used to help visualize the damaged bone region, and to track the process of inserting the access cannula, trocar, and other tools. Once the access cannula is near the damaged bone region, a bone drill may be used to drill into the bone, as shown in FIG. 7C.

Figure 7C:
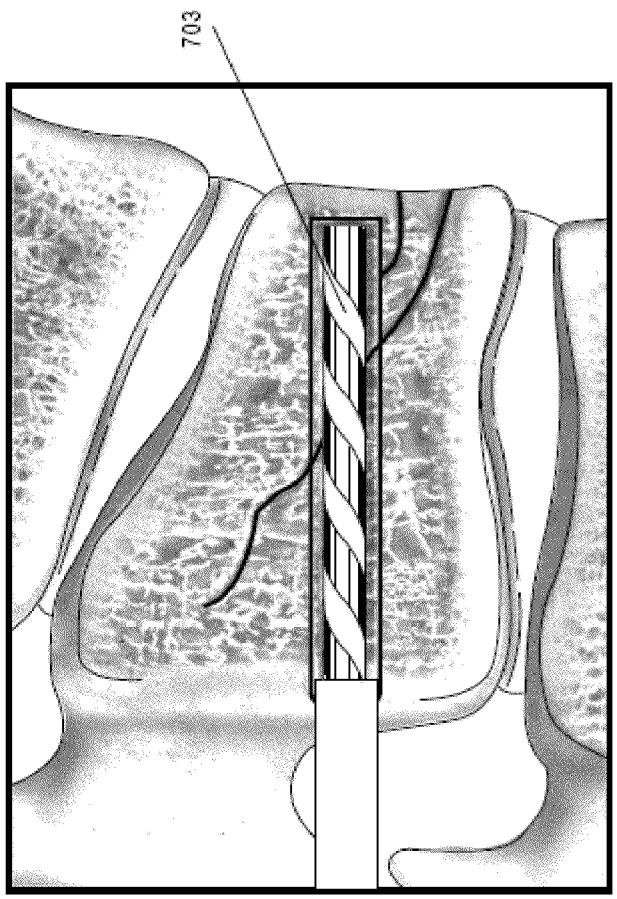
Figure 7D:
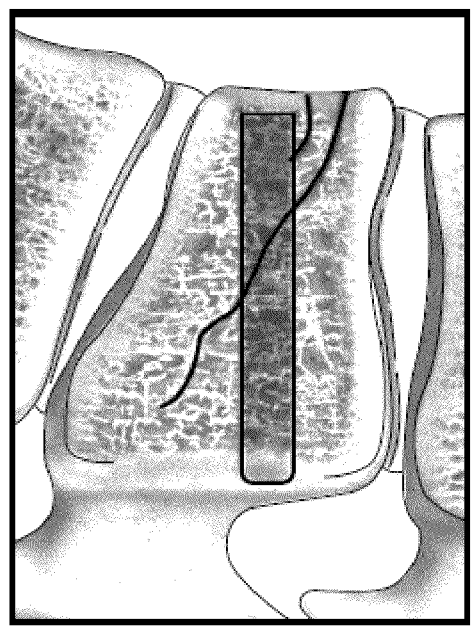
Figure 7E:
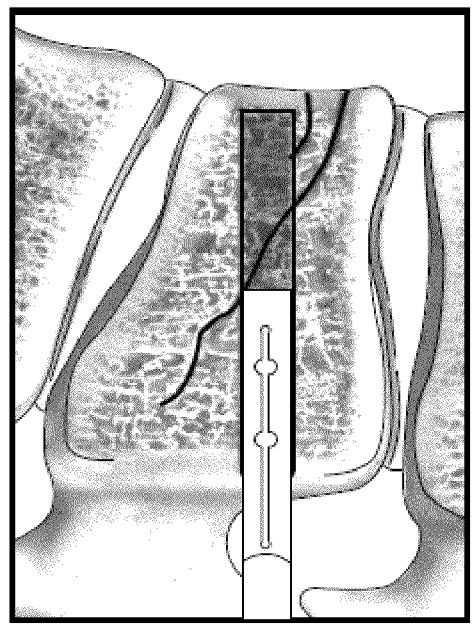
Figure 8:
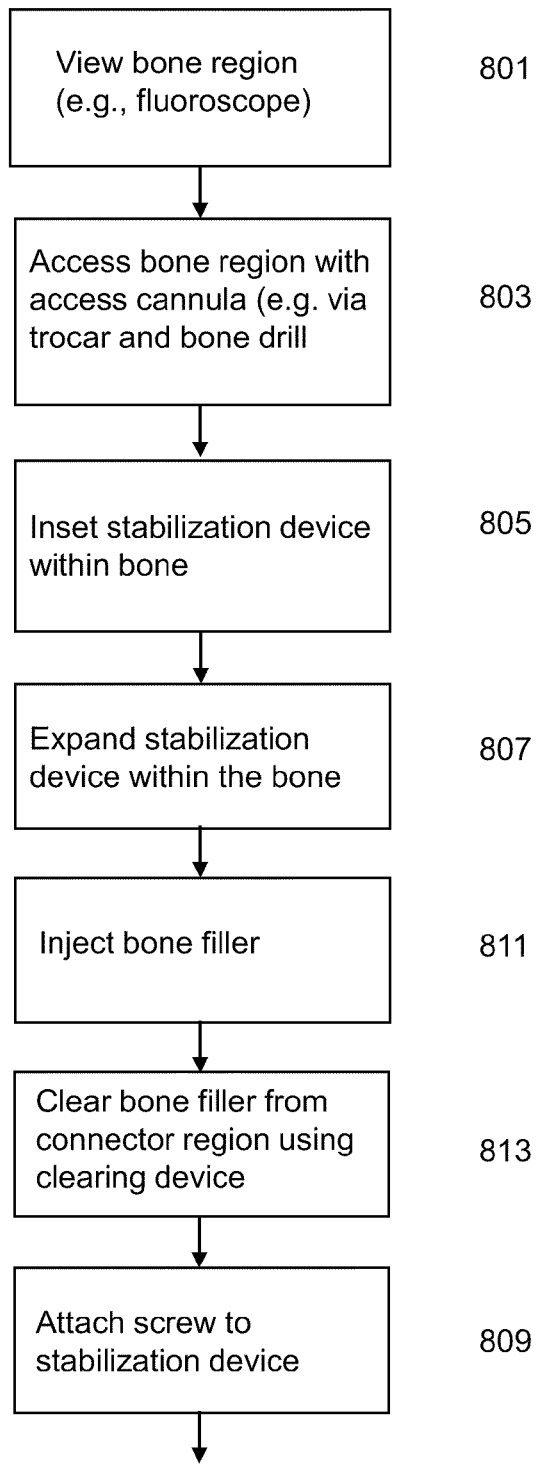
FIG. 8 is a schematic flowchart illustrating one method of treating a bone using the devices and described herein.

In FIG. 7C the drill 703 enters the bone from the access cannula. The drill enters the cancellous bony region within the vertebra. After drilling into the vertebra to provide access, the drill is removed from the bone and the access cannula is used to provide access to the damaged vertebra, as shown, by leaving the access cannula in place, providing a space into which the stabilization device may be inserted in the bone, as shown in FIG. 7D. In FIG. 7E a stabilization device, attached to an inserter and held in the delivery configuration, is inserted into the damaged vertebra.

Figure 7G:
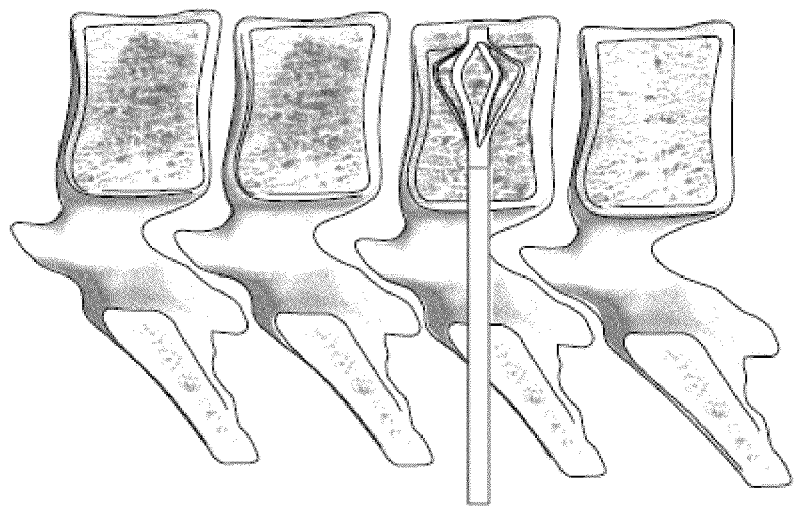
Figure 7F:
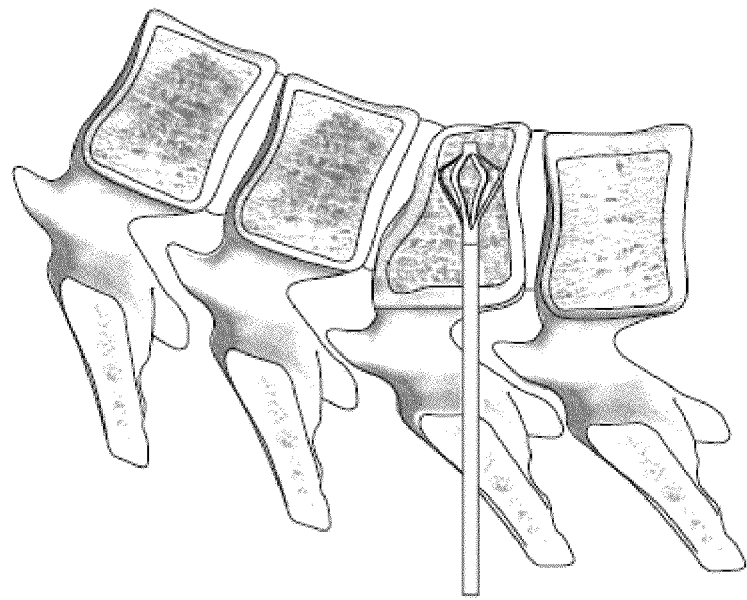

Once in position within the vertebra, the stabilization device is allowed to expand (by self-expansion) within the cancellous bone of the vertebra, as shown in FIG. 7F. In some variations, the device may fully expand, cutting through the cancellous bone and pushing against the cortical bone with a sufficient restoring force to correct the compression, as shown in FIG. 7G. However, in some variations, the force generated by the device during self-expansion is not sufficient to distract the bone, and the inserter handle may be used (e.g., by applying force to the handle, or by directly applying force to the proximal end of the inserter) to expand the stabilization device until the cortical bone is sufficiently distracted.

After the stabilization device has been positioned and is expanded, it may be released from the inserter. In some variations, it may be desirable to move or redeploy the stabilization device, or to replace it with a larger or smaller device. If the device has been separated from the inserter (e.g., by detaching the removable attachments on the stabilization device from the cooperating attachments on the inserter), then it may be reattached to the inserter. Thus, the distal end of the inserter can be coupled to the stabilization device after implantation. The inserter can then be used to collapse the stabilization device back down to the delivery configuration (e.g., by compressing the handle in some variation), and the device can be withdrawn or re-positioned.

Once the device has been correctly positioned in the bone, a bone screw may be inserted in the same pathway formed to insert the stabilization device, as shown in FIG. 7H (arrow). The bone screw may engage the bone screw attachment region of the stabilization device and be secured by the stabilization device within the bone. As previously mentioned, bone cement may also be used (e.g., inserted into the bone stabilization device prior to adding the bone screw) to further stabilize the bone screw. Once the bone screw has engaged the stabilization device in the bone screw attachment region, it may be secured in position (e.g., by screwing). As shown in FIG. 7I, the bone screw is then secured in the bone by virtue of the association with the stabilization device.

Implant Thread Clearing

Figure 7J:
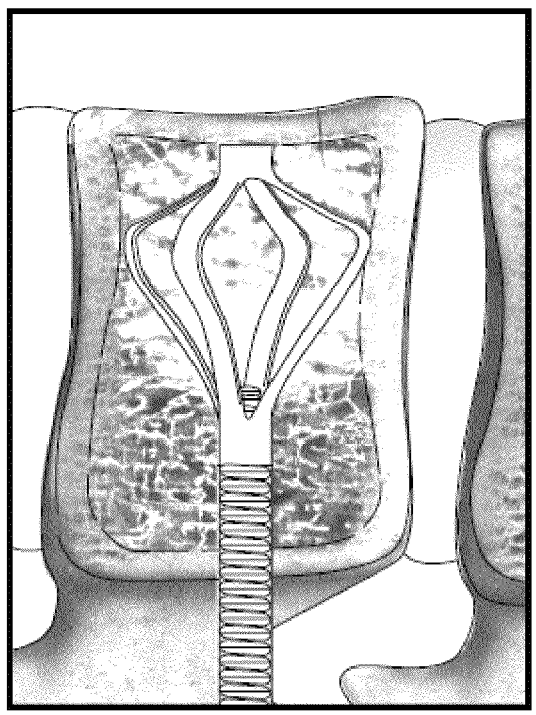

In variations in which a cement (e.g., a bone cement) or bone filling material is added to the stabilization device, as shown in FIG. 7J, a clearing device may also be used. It should also be noted that any of the clearing devices described herein may also be used without using a bone cement/filler.

For example, a clearing device may be used to remove blood or tissue which may become lodged in the connection region during implantation.

Figure 9A:
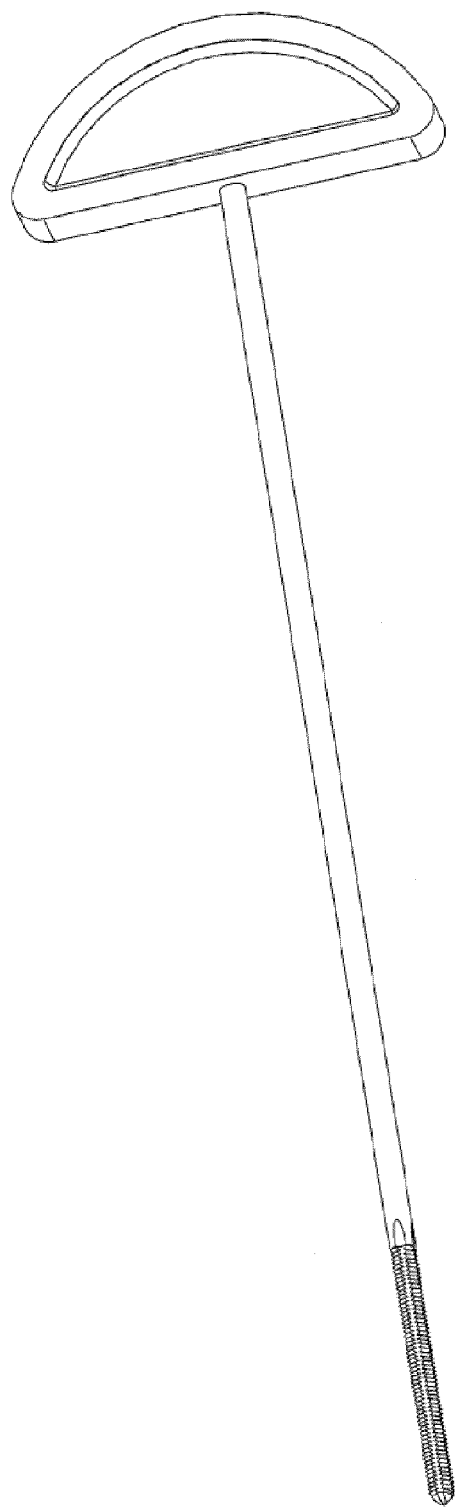
FIG. 9A is one example of a clearing device.
Figure 9B:
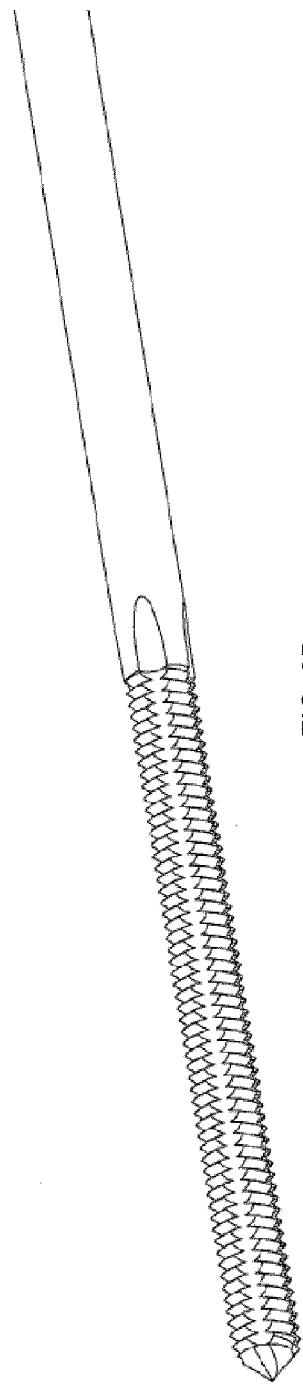
FIGS. 9B and 9C show enlarged perspective views of the distal and proximal ends of this device.
Figure 9C:
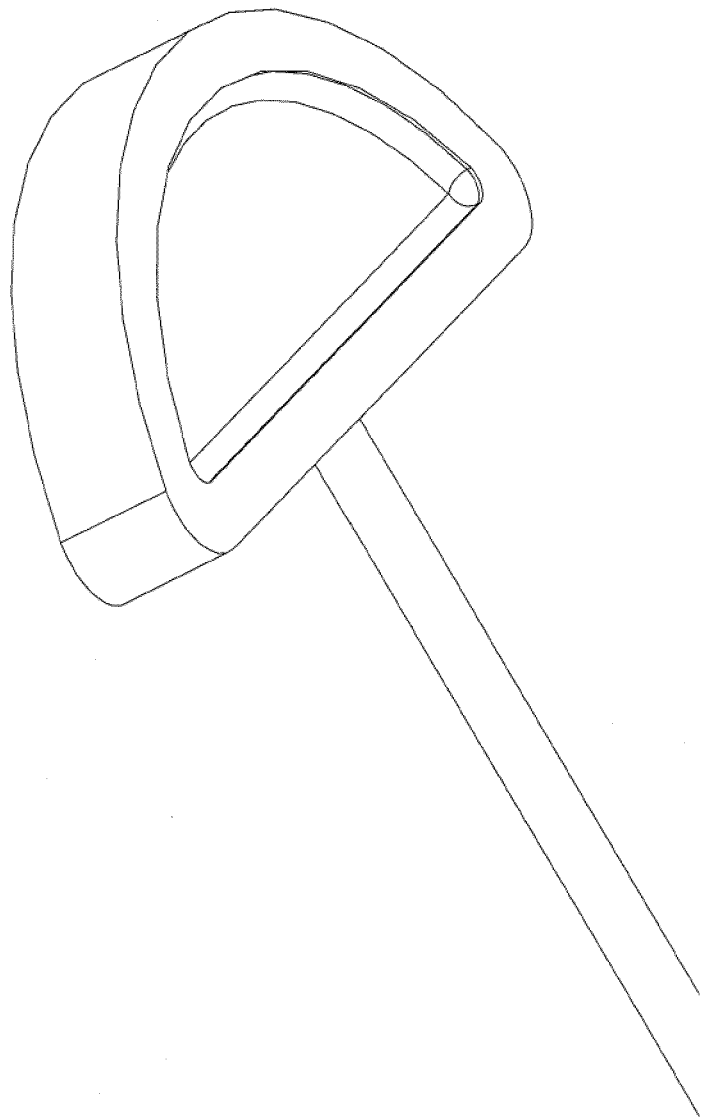

FIG. 9A illustrates one variation of a clearing device. In this example, the device is configured as a threaded bone filling material plunger. This device is configured as a threaded bone filling material plunger. The distal end (tip region) of this device is configured to engage the connector region (attachment region) of the stabilization device. In this example, the tip of the clearing device is threaded to engage the connector region of the stabilization device, and has the same diameter (i.e. screw number or metric dimension) and pitch as the proximal end of the implant. Thus, the tip may thread into the implant. The tip may be fabricated from a metal, ceramic, or other material that is harder than the (cured) bone filler (e.g., PMMA). The tip region may also be made of a material that is capable of holding a sharp edge. The material may also be biocompatible, and/or radio-opaque.

In some variations, the distal tip of this region may be pointed or inclined, so that it can self-center within the connector region.

In some variations, the clearing device also includes a passageway or channel for removal of material. For example, in FIG. 9A (and also shown in FIG. 9B), the distal end of the device has longitudinal flutes to allow the material being cleared to be removed by the device. For example, material removed from the attachment region may be forced in the opposite axial direction along the channel of the clearing device (in the manner of an Archimedes' screw). Two or more flutes may be included. The ratio of total threaded arc length to total fluted arc length at a cross section orthogonal to the longitudinal axis is preferentially 1:1, but may vary based on the tip material, the implant threading (diameter and pitch), the degree of PMMA incursion into implant threads, the requisite speed of PMMA removal, properties of a particular PMMA formulation, and/or torque generated on the implant, along the shaft, or at the handle The shape and configuration of the distal end of the device is configured to remove (by scraping, scratching, wiping, etc.) material from the connector or attachment region of the stabilization device. For example, the exterior edges of the tip threading may be preferentially sharp and V-shaped, rather than a rounded V, as allowed by relevant national and international standards.

The shaft region of the threaded bone filling material plunger in this example extends from the distal end to the proximal end (having a handle). The shaft region may be made of the same or different material as the tip. In some variations, the tip region is permanently attached to the shaft; alternatively the tip region maybe separable from the shaft. The shaft may be rigid or moderately flexible. The proximal end of the shaft may terminate in some a handle at the distal end of the device. The handle may include a grip or grasping region, including one or more surfaces so that force can be applied to push the device distally or withdraw it proximally and/or rotate the device axially.

Figure 10A:
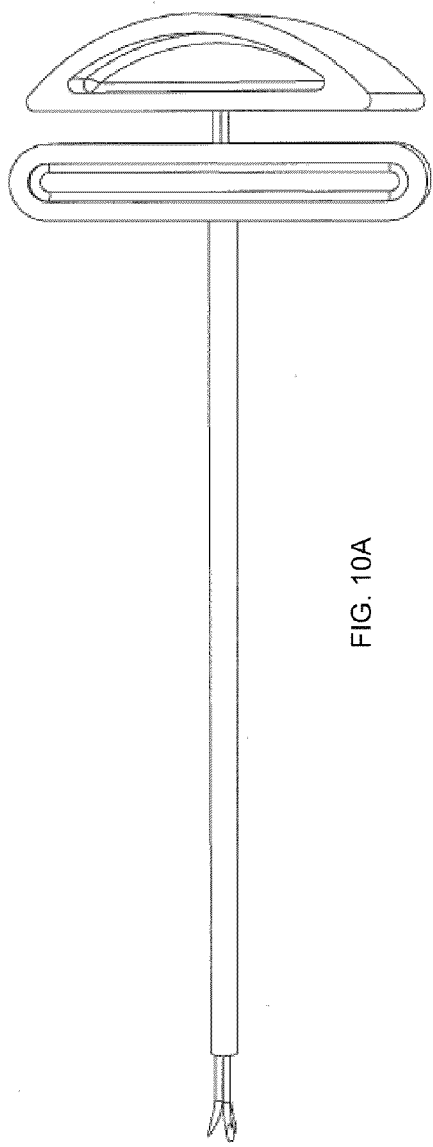
FIG. 10A is a side view of another example of a clearing device.

FIG. 10A shows another variation of a clearing device. This variation of a clearing device includes a rigid (or minimally flexible) elongate portion (e.g., tube) and a movable abrading or scraping portion at the distal end. In FIG. 10A, the rigid elongate portion is configured as a rigid or minimally flexible tube having a central passageway and a first handle. The movable abrading or scraping portion is configured as a plurality of rods which are slidable and/or rotatably movable through the central passageway of the elongate portion. These rods may be individual (e.g. separate) along all or a portion of their length, or they may be coupled together at some point along their length (e.g., near the distal end). The abrading portion is also connected to a handle (second handle). The first and second handles may move independently of each other. The abrading portion in this variation comprises three elongate rods connected to the second handle. In other variations any number of rods (including just one rod) may be used. The distal end of the tube may be a simple 'square' cut or it may be shaped (e.g. flared, swaged, or, most likely, tapered). The tube (e.g., with the abrasive region withdrawn into the passageway of the tube) may be advanced into the tissue to follow the path taken during insertion of the stabilization device.

The rod or rods forming the abrasive portion may be positioned within the tube so that their longitudinal positions relative to each other and/or relative to the tube can be changed. The rods may be pre-shaped (e.g., pre-biased) or may be guided by the tube or elements in the tube such that their distal tips are directed radially outward when extended from the tube. The rod tips may be square cut, but are likely preferentially sharpened. In some variations, rather than multiple rods, the abrasive region of the device may be formed from a single rod that has one or more tips at its distal end. One or more of the rods may be hollow, or may include a passage for the application or removal of material (e.g., vacuum passage).

Figure 10C:
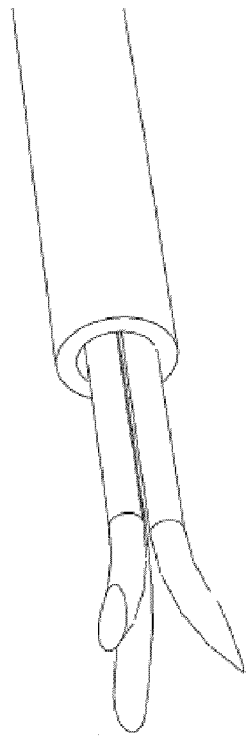
FIG. 10C shows an enlarged view of the distal end of the device of FIGS. 10A and 10B.

As illustrated in FIG. 10C, the sizes of the tube and the abrasive region may be configured so that there is sufficient clearance between tube inner diameter (ID) and rod outer diameter (OD), so that the latter can rotate easily within the former. In some variations, the tube OD to rod ID should not be a large multiple. The length of the abrasive region may be matched to the length of the outer rod, so that the distance the rod tips(s) extend beyond the tube OD is preferably short. In some variations, if the rod is too small and/or if its tip(s) extend too far from the tube, there may not be insufficient rigidity to remove the bone cement from the threading. Thus, the rods may extend only slightly from the distal end (e.g., less than 10 mm, less than 5 mm, less than 3 mm, etc.).

Figure 10B:
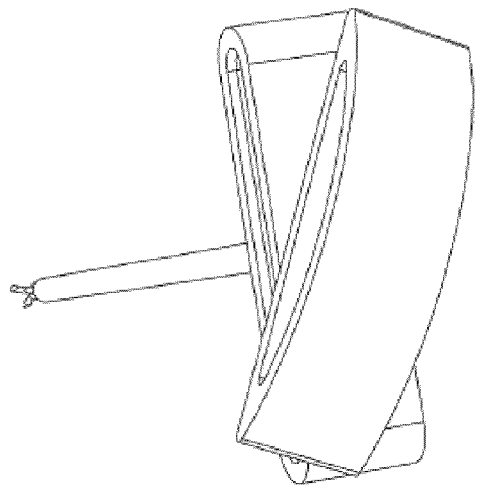
FIG. 10B shows a top perspective view of the same device shown in FIG. 10A.

In operation, the device shown in FIGS. 10A-10C may be used by first advancing the tube to the connector region of the stabilization device. For example, the clearing device may be extended into the subject so that the tube is within or adjacent to the threaded connector region (in variations in which the connector region is threaded). In particular, in this example, the device may be extended into the connector region of the stabilization device without engaging the connector region. For example, the tube (outer tube) of a clearing device may have an outer diameter that is less than the inner diameter of the connector region. The distal end of the device may be extended into the region of the device that is occluded or contaminated with bone filler (e.g., cement). The abrasive region (e.g., rods) may then be advanced from out of the tube until their tips exit the distal end of the tube and pass into the connector region of the stabilization device (e.g., threading). The rods or the rod/tube assembly may then be rotated about the longitudinal axis using the handles at the proximal end. The rod tips may scrape or otherwise remove the cement from the threading. As mentioned, in some variations a suction port may be included to remove some or all of the material scraped from the connector region.

FIG. 8 shows a flowchart summarizing a method for repairing a bone, as described herein. For example, the bone region into which the stabilization device and bone screw are to be inserted may first be visualized (e.g., using a fluoroscope or other appropriate visualization technique) 801. The bone region can then be accessed using an access cannual (e.g., a trocar and/or drill) 803 to form a cavity into which the stabilization device can be inserted. The location (e.g., position, depth, etc.) of the stabilization device can be determined with respect to the eventual addition of the bone screw. Thus, the angle into which the stabilization device is inserted my partially determine the angle that the proximal end of the bone screw presents. Once the bone has been prepared, the stabilization device can be inserted 805 into the bone, and allowed to expand 807. As mentioned, additional force may be applied to help position and further expand the device. Once the device is expanded, additional support material (e.g., fluent bone cement, etc.) may be added if desired 811. The connecting region of the implanted stabilization device may then be cleaned using a clearing device 813, as described briefly above. For example, a threaded bone filling material plunger may be threaded into the connector region of the device to remove any bone filler. After removing the threaded bone filling material plunger, a bone screw may then be attached by mating the bone screw with the bone screw attachment region (connector region) of the self-expanding stabilization device 809. The final depth and position of the bone screw (as well as any additional structures such as plates, screws, etc.) may be adjusted by altering the level to which the bone screw is inserted into the stabilization device, etc.

The methods described herein outline only one example of the use of the devices described herein, and additional variations may be included. While embodiments of the present invention have been shown and described herein, such embodiments are provided by way of example only. Thus, alternatives to the embodiments of the invention described herein may be employed in practicing the invention. The exemplary claims that follow help further define the scope of the systems, devices and methods (and equivalents thereof).

What is claimed is:

1. A method of preparing the mating region of a bone stabilization implant for coupling with a secondary implant such as a bone screw, the method comprising: inserting a bone stabilization device into a bone, the bone stabilization device having a proximal connector; allowing the bone stabilization device to self-expand within the bone; injecting a bone filler in and around the bone stabilization device; and clearing bone filler from the connector region of the bone stabilization device using a clearing device, the clearing device comprising an elongate member having a proximal handle and a distal cleaning region.

2. The method of claim 1, further comprising attaching a secondary implant to the bone stabilization device.

3. The method of claim 1, further comprising screwing a bone screw into the connector region of the bone stabilization device.

4. The method of claim 1, wherein step of inserting the bone stabilization device comprises inserting a bone stabilization device having a tubular elongate body and a plurality of self-expanding struts configured to extend therefrom.

5. The method of claim 1, wherein the step of allowing the bone stabilization device to self-expand comprises controlling the self-expansion of one or more struts of the bone stabilization device.

6. The method of claim 1, wherein the step of injecting a bone filler in and around the bone stabilization device comprises injecting a bone cement.

7. The method of claim 1, further comprising allowing the bone filler to set before of clearing bone filler from the connector region.

8. The method of claim 1, wherein the step of clearing bone filler from the connector region comprises coupling the distal clearing region of the clearing device to the connector region of the bone stabilization device.

9. The method of claim 1, wherein the step of clearing bone filler from the connector region comprises scraping an edge region of the distal clearing region against the connector region.

10. The method of claim 1, wherein the step of clearing bone filler from the connector region comprises applying suction to remove bone filler.

11. A method of cleaning a treaded connector of a bone stabilization implant so that it may mate with a secondary implant such as a bone screw, the method comprising: inserting a bone stabilization implant into a bone, wherein the bone stabilization implant includes a threaded proximal region and a plurality of self-expanding struts; allowing the struts of the bone stabilization implant to self-expand within the bone; injecting a bone filler in and around the bone stabilization device; and clearing bone filler from the threaded proximal region of the bone stabilization device using a clearing device, the clearing device comprising an elongate member having a proximal handle and a distal clearing region configured to mate with the threaded proximal region of the bone stabilization implant.

12. The method of claim 11, further comprising attaching a secondary implant to the bone stabilization device.

13. The method of claim 11, further comprising screwing a bone screw into the threaded proximal region of the bone stabilization device.

14. The method of claim 11, wherein the step of allowing the bone stabilization device to self-expand comprises controlling the self-expansion of one or more of the struts of the bone stabilization device.

15. The method of claim 11, wherein the step of injecting a bone filler in and around the bone stabilization device comprises injecting a bone cement.

16. The method of claim 11, further comprising allowing the bone filler to set before of clearing bone filler from the connector region.

17. The method of claim 11, wherein the step of clearing bone filler from the threaded proximal region comprises scraping an edge region of the distal clearing region against the connector region.

18. The method of claim 11, wherein the step of clearing bone filler from the connector region comprises applying suction to remove bone filler.

19. A kit for implanting a bone stabilization device and a secondary implant configured to couple to the bone stabilization device, the kit comprising: a bone stabilization device comprising: a tubular elongate body and a plurality of self-expanding struts configured to extend therefrom, wherein the plurality of self-expanding struts are configured to cut through cancellous bone; a proximal connector region configured to connect to a secondary implant; a distal connector region configured to connect to the distal end of an inserter; and a clearing device for clearing the proximal connector region of the self-expanding bone stabilization device, the clearing device comprising: a proximal handle; an elongate shaft coupled to the proximal handle; and a distal cleaning region configured to mate with a proximal connector region of a bone stabilization device to remove bone filler from the proximal connector region.

20. The kit of claim 19, wherein the clearing device comprises a vacuum port at the distal cleaning region.

* * * * *